US006852491B2

(12) United States Patent
Harris et al.

(10) Patent No.: US 6,852,491 B2
(45) Date of Patent: Feb. 8, 2005

(54) AMPLIFICATION AND DETECTION REAGENTS FOR HIV-1

(75) Inventors: Barbara J. Harris, Gurnee, IL (US); John R. Hackett, Jr., Libertyville, IL (US); Priscilla Swanson, Libertyville, IL (US); Klara Abravaya, Wilmette, IL (US); Sushil G. Devare, Northbrook, IL (US); Jacek J. Gorzowski, Mundelein, IL (US); Claudia A. Esping, Geneva, IL (US); Ning Tang, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/945,943

(22) Filed: Sep. 4, 2001

(65) Prior Publication Data

US 2003/0148280 A1 Aug. 7, 2003

(51) Int. Cl.[7] .................................................. C12Q 1/68
(52) U.S. Cl. ............................ 435/6; 435/5; 536/23.72; 536/24.32
(58) Field of Search .............................. 435/5, 6, 974; 536/23.72, 24.32

(56) References Cited

U.S. PATENT DOCUMENTS

| 4,683,195 A | 7/1987 | Mullis et al. |
| 4,683,202 A | 7/1987 | Mullis |
| 4,948,882 A | 8/1990 | Ruth |
| 5,034,506 A | 7/1991 | Summerton et al. |
| 5,142,047 A | 8/1992 | Summerton et al. |
| 5,185,444 A | 2/1993 | Summerton et al. |
| 5,210,015 A | 5/1993 | Gelfand et al. |
| 5,310,652 A | 5/1994 | Gelfand et al. |
| 5,322,770 A | 6/1994 | Gelfand |
| 5,399,491 A | 3/1995 | Kacian et al. |
| 5,424,414 A | 6/1995 | Mattingly |
| 5,464,746 A | 11/1995 | Fino |
| 5,686,272 A | 11/1997 | Marshall et al. |
| 5,925,517 A | 7/1999 | Tyagi et al. |
| 5,962,665 A | 10/1999 | Kroeger et al. |

FOREIGN PATENT DOCUMENTS

| WO | WO/92 20702 | 11/1999 |
| WO | 01/46404 A1 * | 6/2001 |

OTHER PUBLICATIONS

Tyagi et al. "Molecular Beacons: Probes that Fluoresce upon Hybridization" Nature Biotechnology, vol. 14, Mar. 1996, pp. 303–308.*
Whitcombe et al. "Detection of PCR products using self–probing amplicons and fluorescence" Nature Biotechnology, vol. 17, Aug. 1999, pp. 804–807.*
Abravaya, K., et al. "Performance of a multiplex qualitative PCR LCx assay for detection of human immunodeficiency virus type 1 (HIV–1) group M subtypes, group O and HIV–2" Journal of Clinical Microbiology, USA 38(3), pp. 716–723 (Feb. 2000).

Alaeus, A., et al. "Subtype–specific problems with quantification of plasma HIV–1 RNA" AIDS, Sweden 11(7), pp. 859–865 (Jun. 1997).
Brennan, C.A., et al. "Sequence of gp41env immunodominant region of HIV type 1 group O from west central Africa" AIDS Research and Human Retroviruses, USA 1;13(10), pp. 901–904 (Jul. 1997).
Brennan, C.A., et al. "Serologic and phylogenetic characterization of HIV–1 subtypes in Uganda" AIDS, USA 11(15), pp. 1823–1832 (Dec. 1997).
Coste, J., et al. "Comparative evaluation of three assays for the quantitation of human immunodeficiency virus type 1 RNA in plasma" Journal of Medical Virology, France 50(4), pp. 293–302 (Dec. 1996).
Debyser, Z., et al. "Failure to quantify viral load with two of the three commercial methods in pregnant woman harboring in HIV type 1 subtype G strain" AIDS Research and Human Retroviruses, Belgium 14(5), pp. 453–459 (Mar. 1998).
Gobbers, E., et al. "Reactivity and amplification efficiency of the NASBA HIV–1 RNA amplification system with regard to different HIV–1 subtypes" Journal of Virological Methods, Belgium 66(2), pp. 293–301 (Jul. 1997).
Hackett, J. Jr., et al. "Genetic analysis of HIV type 1 group O p 24gag sequences from Cameroon and Equatorial Guinea" AIDS Research and Human Retroviruses, USA 13(13), pp. 1155–1158 (Sep. 1997).
He, Q., et al. "Primers are decisive for sensitivity of PCR" Biotechniques, Finland 17(1):82, pp. 84, 86–87 (Jul. 1994).
Holguin, A., et al. "Comparison of three different commercial methods for measuring plasma viraemia in patients infected with non–B HIV–1 subtypes" European Journal of Clinical Microbiology and Infectious Diseases, Spain 18(4), pp. 256–259 (Apr. 1999).
Jackson, J. B., et al. "Detection of Human Immunodeficiency Virus Type 1 (HIV–1) DNA and RNA Sequences in HIV–1 Antibody–Positive Blood Donors in Uganda by the Roche AMPLICOR Assay", Journal of Clinical Microbiology, USA 35(4), pp. 873–876 (Apr. 1997).
Johanson, J., et al. "A new ultrasensitive assay for quantitation of HIV–1 RNA in plasma" Journal of Virological Methods, USA 95(1–2), pp. 81–92 (Jun. 2001).
Kern, D., et al. "An enhanced–sensitivity branched–DNA assay for quantification of human immunodeficiency virus type 1 RNA in plasma", Journal of Clinical Microbiology, USA 34(12), pp. 3196–3202 (Dec. 1996).
Kievits, T., et al. "NASBA isothermal enzymatic in vitro nucleic acid amplification optimized for the diagnosis of HIV–1 infection", Journal of Virological Methods, The Neatherlands 35(3), pp. 273–286 (Dec. 1991).

(List continued on next page.)

*Primary Examiner*—Jeffrey Stucker
(74) *Attorney, Agent, or Firm*—William E. Murray

(57) ABSTRACT

Oligonucleotide primer sets, probes, and combinations of the primer sets and probes are provided herein. These reagents are useful for amplifying and detecting HIV-1 target sequences in a test sample.

8 Claims, 11 Drawing Sheets

OTHER PUBLICATIONS

Loussert–Ajak, I., et al. "Genetic diversity and HIV detection by polymerase chain reaction" Lancet 346(8988), pp. 912–913 (Sep. 1995).

Mulder, J., et al. "Rapid and simple PCR assay for quantitation of human immunodeficiency virus type 1 RNA in plasma: application to acute retroviral infection", Journal of Clinical Microbiology, USA 32(2), pp. 292–300 (Feb. 1994).

Ou, C–Y., et al. "DNA Amplification for direct Detection of HIV–1 in DNA of Peripheral Blood Mononuclear Cells", Science 239 (4837), pp. 295–297 (Jan. 1988).

Repress, R.A., et al. "Detection of genetically diverse human immunodeficiency virus type 1 group M and O isolates by PCR", Journal of Clinical Microbiology, USA 35(5), pp. 1284–1286 (May 1997).

Segondy, M., et al. "Evaluation of the Nuclisens HIV–1 QT assay for quantitation of human immunodeficiency virus type 1 RNA levels in plasma" Journal of Clinical Microbiology, France 36(11), pp. 3372–3374 (Nov. 1998).

Swanson, P., et al. "Comparative performance of three viral load assays on human immunodeficiency virus type 1 (HIV–1) isolates representing group M (subtypes A to G and group O: LCx HIV RNA quantitative, AMPLICOR HIV–1 Monitor version 1.5, and Quantiplex HIV–1 RNA version 3.0" Journal of Clinical Microbiology, USA 39(3), pp. 862–870 (Mar. 2001).

Swanson, P., et al. "Quantification of HIV–1 group M (subtypes A–G) and group O by the LCx HIV RNA quantitative assay", Journal of Virological Methods, USA 89(1–2), pp. 97–108 (Sep. 1989).

Vandamme, A.M., et al. "Quantification of HIV–1 RNA in plasma: comparable results with eh NASBA HIV–1 RNA QT and the AMPLICOR HIV monitor test" Journal of Acquired Immune Deficiency Syndromes Belgium 13(2), pp. 127–139 (Oct. 1996).

* cited by examiner

AMPLIFICATION AND DETECTION REAGENTS FOR HIV-1

FIELD OF THE INVENTION

The present invention relates to Human Immunodeficiency Virus Type 1 (HIV-1). In particular the invention relates to methods of amplifying and detecting HIV-1 nucleic acid sequences.

BACKGROUND OF THE INVENTION

Molecular characterization of HIV-1 strains collected from around the world has revealed extensive genetic diversity. Based on phylogenetic analysis of viral genomic sequences, HIV-1 has been divided into three distinct groups, M, N and O. Group M viruses represent the majority of HIV-1 and based on sequence divergence have been further subdivided into nine distinguishable clades, designated subtypes A, B, C, D, F, G, H, J, and K (Robertson, D. L. et.al. In: *Human Retroviruses and AIDS* 1999-*A Compilation and Analysis of Nucleic Acid and Amino Acid Sequences*, Kuiken, C. et. al. Eds., pgs. 492–505 (1999)). The phylogenetic pattern for group M isolates has been described as a star phylogeny with the subtypes roughly equidistant from each other while diverging from a common ancestor. For viral envelope (env) gene amino acid sequences, the degree of intrasubtype divergence ranges up to 20% and the intersubtype divergence is 25–30% (Sharp, P. M. et.al., AIDS 8: S27–S42 (1994)).

In 1990, an unusual HIV-1 strain (ANT70) isolated from a Cameroonian patient was reported (De Leys, R. et. al., J. Virol. 64:1207–1216 (1990)). Based on the available sequence information, this strain of virus appeared to be very different from other HIV-1 sequences. A similar virus (MVP-5180) was isolated from a second Cameroonian patient (Gürtler, L. et. al., J. Virol. 68:1581–1585 (1994)). Complete genome sequencing revealed that although these viruses shared the same overall genomic structure with group M strains, their sequences were highly divergent having only ~50% nucleotide homology within the env gene as compared to group M isolates (Gürtler, L. et. al., J. Virol. 68:1581–1585 (1994)). Due to the extent of genetic divergence from group M strains, these isolates were designated as group O (outlier) viruses. More recently, HIV-1 viruses that are phylogenetically equidistant from group M and group O strains have been identified in Cameroon; these have been designated as group N (Simon, F. et. al., Nat. Med. 4:1032–1037 (1998)).

An innately error-prone reverse transcriptase enzyme, high viral loads and in vivo selective pressure all contribute to the genetic diversity of HIV-1. An additional source of diversity is a by-product of the HIV replicative cycle where two genomic RNA transcripts linked at their 5' ends are encapsidated into a virion. If a cell is simultaneously infected with more than one HIV-1 strain, heterozygous virions can be produced. Subsequent to infection with the virion, reverse transcriptase can switch back and forth between the two RNA transcripts, generating a recombinant virus (Hu, W. S. and H. M. Temin, Science 250:1227–1233 (1990)). This capacity to recombine provides an opportunity for rapid and dramatic genetic change. A naturally-occurring intersubtype recombinant virus was first identified by Sabino and colleagues who characterized a B/F mosaic found in two epidemiologically linked patients (Sabino, E. C. et. al., J. Virol. 68:6340–6346 (1994)). In areas where multiple subtypes co-circulate, intersubtype recombinants may account for 20% or more of HIV-1 infections (Cornelissen, M. et. al., J. Virol. 70:8209–8212 (1996)). Although the majority of viral recombinants described to date are group M intersubtype mosaics, intergroup recombinant viruses composed of group M and group O gene segments have also been identified (Peeters, M. et. al., J. of Virol. 73:7368–7375 (1999)).

Characterization of full-length genomes revealed that reference strains for two previously recognized subtypes of group M were actually intersubtype recombinant viruses. All representatives of "subtype E" strains sequenced to date consist of gag and RNA dependent DNA polymerase (pol) genes from subtype A while their env gene is derived from subtype E (Gao, F. et. al., J. Virol. 70:7013–7029 (1996)). HIV-1 strains previously recognized as subtype I strains have since been shown to be triple mosaics consisting of subgenomic segments derived from subtypes A, G and I (Nasioulas, G. et. al., AIDS Res. Hum. Retroviruses 15:745–758 (1999)). Such recombinant strains with evidence of epidemic spread have been classified as Circulating Recombinant Forms (CRF; Robertson, D. L. et.al. In: *Human Retroviruses and AIDS* 1999-*A Compilation and Analysis of Nucleic Acid and Amino Acid Sequences*, Kuiken, C. et. al. Eds., pgs. 492–505 (1999)).

The potential for emergence of CRF strains is well documented. Subtype E strains, designated CRF01_AE, are the predominant form of HIV-1 in Thailand. In Kaliningrad, an outbreak of an A/B recombinant virus (CRF03_AB) has recently been documented in injecting drug users (Liitsola, K. et. al., AIDS 12:1907–1919 (1999)). An A/G intersubtype recombinant with a unique and complex mosaic pattern (CRF02_AG), has been identified in Nigeria, Djibouti and regions of west central Africa (Carr, J. K. et. al., Virology 247:22–31 (1998)).

The overall distribution of HIV-1 groups, subtypes and CRFs varies considerably in different geographic regions and is undergoing continual change. While subtype B is predominant in North America and Western Europe (McCutchan, F. E., AIDS 14 (suppl 3): S31–S44 (2000)), increasing numbers of non-subtype B infections are being observed in both Europe and the United States. In France, over the 10-year period from 1985–1995, the prevalence of non-B viruses increased from approximately 4% to more than 20% (Barin, F. et. al., AIDS 11:1503–1508 (1997)). Non-B reactive specimens were found in almost all regions tested. Remarkably, nearly every group M subtype and group O infections were reported at a single hospital in Paris (Simon, F. et. al., AIDS Res. Hum. Retroviruses 15:1427–1433 (1996)). Analysis of 24 recently infected German patients revealed that 33% were infected with non-B viruses; these included subtypes A, E and C (Dietrich, U. et. al., AIDS 11:1532–1533 (1997)). In Belgium, subtype A, C, D, E, F, G and H infections were detected, accounting for more than 30% of total HIV-1 infections (Heyndrickx, L. et. al., AIDS Res. Hum. Retroviruses 14:1291–1296 (1998)). Increasing numbers of non-subtype B infections, including subtypes A, D, E, F and group O, are also being detected in the United States (Weidle, P. J. et. al., J. Infect. Dis. 181:470–475 (2000). Thus, viral heterogeneity is increasing in regions in which subtype B was traditionally most prevalent.

Quantification of virion-associated RNA in plasma has become a well-established method for clinical management and follow-up of patients with HIV-1 infection. A variety of nucleic acid-based techniques have been developed for detection and quantification of HIV-1 viral RNA including, reverse transcriptase-coupled polymerase chain reaction (RT-PCR), nucleic acid sequence-based amplification (NASBA), and branched DNA (bDNA) (Mulder, J. et. al., J. Clin. Microbiol. 32:292–300 (1994); Kievits, T. et. al., J. Virol. Methods 35:273–286 (1991); Kern, D. et. al., J. Clin. Microbiol. 34:3196–3202 (1996); Swanson P. et. al., J. Virol. Methods 89:97–108 (2000)). These techniques all rely on hybridization of oligonucleotides to the target sequences. Mismatches between the primers/probes and target sequences have the potential to abolish or reduce the efficiency of amplification and/or detection of the targeted sequences. Thus, selection of primer and/or probe sequences plays a critical role in the performance of these assays.

The original nucleic acid-based tests were developed based primarily on sequence information derived from HIV-1 subtype B common to the United States and Western Europe. The influence of HIV-1 genetic diversity on the efficiency of amplification by the first-generation Amplicor HIV-1 Monitor (version 1.0) assay soon became evident as it failed to detect or underquantified group M subtype A, E, F, G and group O clinical specimens and viral isolates (Loussert-Ajaka, I. et. al., Lancet 346:912–913 (1995); Coste, J. et. al., J. Med. Virol. 50:293–302 (1996); Swanson P. et. al. J. Virol. Methods 89:97–108 (2000)). Mismatches due to HIV-1 genetic diversity were also shown to affect quantification of group M subtype A, G, H, J, and group O specimens by the NASBA HIV-1 RNA QT test (Coste, J. et. al., J. Med. Virol. 50:293–302 (1996); Vandamme, A-M. et. al., J. Acquired Immune Defic. Syndr. Hum. Retrovirol. 13:127–139 (1996); Debyser, Z. et. al., AIDS Res. Hum. Retroviruses 14:453–459 (1998)). Intrasubtype diversity also impacts these assays as both the Amplicor HIV-1 Monitor and the NASBA HIV RNA QT test underquantified genetically divergent subtype B specimens (Alaeus, A. et. al., AIDS 11:859–865 (1997); Gobbers, E. et. al., J. Virol. Methods 66:293–301 (1997)). The influence of HIV-1 genetic diversity on assay performance was still evident even on second-generation versions of the RT-PCR, NASBA and bDNA assays (Segondy, M. et. al., J. Clin. Microbiol. 36:3372–3374 (1997); Holguin A., et. al., Eur. J. Clin. Microbiol. Infect. Dis. 18:256–259 (1999)). The current Amplicor Monitor 1.5 test shows marked improvement on group M subtypes, but fails to detect or quantifies unreliably, group O specimens (Swanson P. et. al., J. Virol. Methods 89:97–108 (2000)). The gag-based NASBA and bDNA assays also fail to detect or underquantify group O specimens (Gobbers, E. et. al., J. Virol. Methods 66:293–301 (1997), Swanson P. et. al., J. Clin. Micro. 39:862–870 (2001)).

Due to the ever-changing geographical distribution of HIV-1 groups and subtypes and the increasing numbers of recombinant forms of HIV-1, it has become critical that assays used to monitor HIV-1 RNA levels in plasma be capable of detecting all HIV-1 variants. Ideally, assays used to quantify HIV-1 viral RNA should function in a group- and subtype-independent manner to ensure reliable quantification of all infections.

Further compounding the difficulty in finding a primer set capable of initially hybridizing with the various groups and subtypes of the highly mutable HIV-1 genome, is the fact that primers selected by comparing them to various genomes are not necessarily effective for amplifying the intended target. As described in He Q., et al., BioTechniques, Vol. 17, No. 1, pp 82–86 (1994), those skilled in the art experience unexplained difficulties obtaining a significant amplification product from primer sets that hybridize to a selected target sequence. This yet to be explained phenomenon has been a challenge facing those designing primer sets for a given target sequence and further complicates the choice of primers for an already difficult HIV-1 target.

There is therefore a need for primer sets and reagents for specifically and sensitively amplifying and detecting HIV-1 variants including those from HIV-1 groups M, N, and O, as well as the various subtypes within or derived from these groups.

SUMMARY OF THE INVENTION

The present invention provides reagents useful for amplifying and detecting all HIV-1 group M, N, and O strains including CRF and inter-group recombinants. In particular, the reagents are in the form of primer sets that can be employed according to nucleic acid amplification procedures to specifically and sensitively detect the HIV-1 variants mentioned above. The primer sets provided herein can be employed according to any of the well known nucleic acid amplification procedures that use a pair of primers to amplify an HIV-1 target sequence. Probe sequences are also provided. The probe sequences can be combined with various primer sets to form oligonucleotide or "oligo" sets that can be used to amplify and detect an HIV-1 target sequence.

Primer sets of the present invention that can be utilized to detect HIV-1 are designated herein as primer set 1 (SEQ. ID. NO. 1 and SEQ. ID. NO. 2); primer set 2 (SEQ. ID. NO. 3 and SEQ. ID. NO. 2); primer set 3 (SEQ. ID. NO. 4 and SEQ. ID. NO. 2); primer set 4 (SEQ. ID. NO. 5 and SEQ. ID. NO. 2); primer set 5 (SEQ. ID. NO. 6 and SEQ. ID. NO. 2); primer set 6 (SEQ. ID. NO. 7 and SEQ. ID. NO. 2); primer set 7 (SEQ. ID. NO. 8 and SEQ. ID. NO. 2); primer set 8 (SEQ. ID. NO. 9 and SEQ. ID. NO. 10); primer set 9 (SEQ. ID. NO. 9 and SEQ. ID. NO. 11); primer set 10 (SEQ. ID. NO. 1 and SEQ. ID. NO. 12); primer set 11 (SEQ. ID. NO. 13 and SEQ. ID. NO. 14); primer set 12 (SEQ. ID. NO. 13 and SEQ. ID. NO. 15); primer set 13 (SEQ. ID. NO. 13 and SEQ. ID. NO. 2); primer set 14 (SEQ. ID. NO. 9 and SEQ. ID. NO. 12); primer set 15 (SEQ. ID. NO. 1 and SEQ. ID. NO. 11); primer set 16 (SEQ. ID. NO. 16 and SEQ. ID. NO. 12); primer set 17 (SEQ. ID. NO. 16 and SEQ. ID. NO. 17); primer set 18 (SEQ. ID. NO. 3 and SEQ. ID. NO. 12); primer set 19 (SEQ. ID. NO. 3 and SEQ. ID. NO. 18); primer set 20 (SEQ. ID. NO. 19 and SEQ. ID. NO. 18); primer set 21 (SEQ. ID. NO. 13 and SEQ. ID. NO. 17); primer set 22 (SEQ. ID. NO. 13 and SEQ. ID. NO. 20); primer set 23 (SEQ. ID. NO. 21 and SEQ. ID. NO. 18); primer set 24 (SEQ. ID. NO. 21 and SEQ. ID. NO. 14); primer set 25 (SEQ. ID. NO. 21 and SEQ. ID. NO. 20); primer set 26 (SEQ. ID. NO. 4 and SEQ. ID. NO. 20); primer set 27 (SEQ. ID. NO. 5 and SEQ. ID. NO. 15); primer set 28 (SEQ. ID. NO. 21 and SEQ. ID. NO. 22); primer set 29 (SEQ. ID. NO. 21 and SEQ. ID. NO. 23); primer set 30 (SEQ. ID. NO. 5 and SEQ. ID. NO. 23); primer set 31 (SEQ. ID. NO. 28 and SEQ. ID. NO. 29); primer set 32 (SEQ. ID. NO. 28 and SEQ. ID. NO. 30); primer set 33 (SEQ. ID. NO. 28 and SEQ. ID. NO. 31); primer set 38 (SEQ. ID. NO. 37 and SEQ. ID. NO. 32); primer set 39 (SEQ. ID. NO. 37 and SEQ. ID. NO. 33); primer set 40 (SEQ. ID. NO. 38 and SEQ. ID. NO. 29); primer set 41 (SEQ. ID. NO. 38 and SEQ. ID. NO. 30); primer set 42 (SEQ. ID. NO. 4 and SEQ. ID. NO. 22); primer set 43 (SEQ. ID. NO. 4 and SEQ. ID. NO. 40); primer set 44 (SEQ. ID. NO. 34 and SEQ. ID. NO. 22); primer set 45 (SEQ. ID. NO. 34 and SEQ. ID. NO. 40); primer set 46 (SEQ. ID. NO. 24 and SEQ. ID. NO. 25); and primer set 47 (SEQ. ID. NO. 26 and SEQ. ID. NO. 27).

The probe sequences provided that may be employed to detect an HIV-1 target sequence (whether amplified or not)

are designated herein as SEQ. ID. NO. 41; SEQ. ID. NO. 42; SEQ. ID. NO. 43; SEQ. ID. NO. 44; SEQ. ID. NO. 45; SEQ. ID. NO. 47; SEQ. ID. NO. 48; SEQ. ID. NO. 49; SEQ. ID. NO. 50; SEQ. ID. NO. 51; SEQ. ID. NO. 52; SEQ. ID. NO. 53; SEQ. ID. NO. 55; SEQ. ID. NO. 57; SEQ. ID. NO. 58; SEQ. ID. NO. 59; SEQ. ID. NO. 60; SEQ. ID. NO. 61; SEQ. ID. NO. 62; SEQ. ID. NO. 63; SEQ. ID. NO. 64; and SEQ. ID. NO. 65.

Oligo sets that can be used to amplify and detect an HIV-1 target sequence are designated herein as oligo set 1 (SEQ. ID. NO. 28, SEQ. ID. NO. 29, and SEQ. ID. NO. 41); oligo set 2 (SEQ. ID. NO. 28, SEQ. ID. NO. 29, and SEQ. ID. NO. 42); oligo set 3 (SEQ. ID. NO. 28, SEQ. ID. NO. 29, and SEQ. ID. NO. 43); oligo set 4 (SEQ. ID. NO. 28, SEQ. ID. NO. 29, and SEQ. ID. NO. 44); oligo set 5 (SEQ. ID. NO. 28, SEQ. ID. NO. 29, and SEQ. ID. NO. 45); oligo set 7 (SEQ. ID. NO. 28, SEQ. ID. NO. 29, and SEQ. ID. NO. 47); oligo set 8 (SEQ. ID. NO. 28, SEQ. ID. NO. 29, and SEQ. ID. NO. 48); oligo set 9 (SEQ. ID. NO. 28, SEQ. ID. NO. 29, and SEQ. ID. NO. 49); oligo set 10 (SEQ. ID. NO. 28, SEQ. ID. NO. 29, and SEQ. ID. NO. 50); oligo set 11 (SEQ. ID. NO. 28, SEQ. ID. NO. 29, and SEQ. ID. NO. 51); oligo set 12 (SEQ. ID. NO. 28, SEQ. ID. NO. 29, and SEQ. ID. NO. 52); oligo set 13 (SEQ. ID. NO. 28, SEQ. ID. NO. 29, and SEQ. ID. NO. 53); oligo set 14 (SEQ. ID. NO. 28, SEQ. ID. NO. 30, and SEQ. ID. NO. 41); oligo set 15 (SEQ. ID. NO. 28, SEQ. ID. NO. 30, and SEQ. ID. NO. 42); oligo set 16 (SEQ. ID. NO. 28, SEQ. ID. NO. 30, and SEQ. ID. NO. 43); oligo set 17 (SEQ. ID. NO. 28, SEQ. ID. NO. 30, and SEQ. ID. NO. 44); oligo set 18 (SEQ. ID. NO. 28, SEQ. ID. NO. 30, and SEQ. ID. NO. 45); oligo set 20 (SEQ. ID. NO. 28, SEQ. ID. NO. 30, and SEQ. ID. NO. 47); oligo set 21 (SEQ. ID. NO. 28, SEQ. ID. NO. 30, and SEQ. ID. NO. 48); oligo set 22 (SEQ. ID. NO. 28, SEQ. ID. NO. 30, and SEQ. ID. NO. 49); oligo set 23 (SEQ. ID. NO. 28, SEQ. ID. NO. 30, and SEQ. ID. NO. 50); oligo set 24 (SEQ. ID. NO. 28, SEQ. ID. NO. 30, and SEQ. ID. NO. 51); oligo set 25 (SEQ. ID. NO. 28, SEQ. ID. NO. 30, and SEQ. ID. NO. 52); oligo set 26 (SEQ. ID. NO. 28, SEQ. ID. NO. 30, and SEQ. ID. NO. 53); oligo set 27 (SEQ. ID. NO. 28, SEQ. ID. NO. 31, and SEQ. ID. NO. 41); oligo set 28 (SEQ. ID. NO. 28, SEQ. ID. NO. 31, and SEQ. ID. NO. 42); oligo set 29 (SEQ. ID. NO. 28, SEQ. ID. NO. 31, and SEQ. ID. NO. 43); oligo set 30 (SEQ. ID. NO. 28, SEQ. ID. NO. 31, and SEQ. ID. NO. 44); oligo set 31 (SEQ. ID. NO. 28, SEQ. ID. NO. 31, and SEQ. ID. NO. 45); oligo set 33 (SEQ. ID. NO. 28, SEQ. ID. NO. 31, and SEQ. ID. NO. 47); oligo set 34 (SEQ. ID. NO. 28, SEQ. ID. NO. 31, and SEQ. ID. NO. 48); oligo set 35 (SEQ. ID. NO. 37, SEQ. ID. NO. 32, and SEQ. ID. NO. 55); oligo set 36 (SEQ. ID. NO. 37, SEQ. ID. NO. 33, and SEQ. ID. NO. 55); oligo set 38 (SEQ. ID. NO. 37, SEQ. ID. NO. 33, and SEQ. ID. NO. 57); oligo set 39 (SEQ. ID. NO. 38, SEQ. ID. NO. 29, and SEQ. ID. NO. 50); oligo set 40 (SEQ. ID. NO. 38, SEQ. ID. NO. 29, and SEQ. ID. NO. 51); oligo set 41 (SEQ. ID. NO. 38, SEQ. ID. NO. 29, and SEQ. ID. NO. 52); oligo set 42 (SEQ. ID. NO. 38, SEQ. ID. NO. 29, and SEQ. ID. NO. 53); oligo set 43 (SEQ. ID. NO. 38, SEQ. ID. NO. 30, and SEQ. ID. NO. 50); oligo set 44 (SEQ. ID. NO. 38, SEQ. ID. NO. 30, and SEQ. ID. NO. 51); oligo set 45 (SEQ. ID. NO. 38, SEQ. ID. NO. 30, and SEQ. ID. NO. 52); oligo set 46 (SEQ. ID. NO. 38, SEQ. ID. NO. 30, and SEQ. ID. NO. 53); oligo set 47 (SEQ. ID. NO. 28, SEQ. ID. NO. 30, and SEQ. ID. NO. 58); oligo set 48 (SEQ. ID. NO. 28, SEQ. ID. NO. 30, and SEQ. ID. NO. 59); oligo set 49 (SEQ. ID. NO. 28, SEQ. ID. NO. 30, and SEQ. ID. NO. 60); oligo set 50 (SEQ. ID. NO. 28, SEQ. ID. NO. 30, and SEQ. ID. NO. 61); oligo set 51 (SEQ. ID. NO. 28, SEQ. ID. NO. 30, and SEQ. ID. NO. 62); oligo set 52 (SEQ. ID. NO. 28, SEQ. ID. NO. 30, and SEQ. ID. NO. 63); oligo set 53 (SEQ. ID. NO. 28, SEQ. ID. NO. 30, and SEQ. ID. NO. 64); and oligo set 54 (SEQ. ID. NO. 28, SEQ. ID. NO. 30, and SEQ. ID. NO. 65).

Methods for amplifying and detecting HIV-1 in a test sample are also provided. Generally, the such methods comprise contacting a test sample with amplification reagents and a previously mentioned primer set to form a reaction mixture. The reaction mixture is then placed under amplification conditions to form an amplification product to thereby amplify the HIV-1 target sequence. Amplification products may be detected using a variety of detection technologies. Preferably, however, an amplification product/probe hybrid is formed and detected as an indication of the presence of HIV-1 in the test sample.

BRIEF DESCRIPTION OF THE DRAWINGS

FIG. 5A shows amplification using primer set #1. Molecular weight bands corresponding to 600, 500 and 1000 bp markers are highlighted with arrows. FIG. 5B shows amplification using primer set #2. Molecular weight bands corresponding to 600 and 1000 bp markers are highlighted with arrows. FIG. 5C shows amplification using primer set #12. Molecular weight bands corresponding to 600 and 1000 bp markers are highlighted with arrows. FIG. 5D shows amplification using primer set #13. The molecular weight band corresponding to the 500 bp marker is highlighted with an arrow.

DETAILED DESCRIPTION OF THE INVENTION

Figure 1:
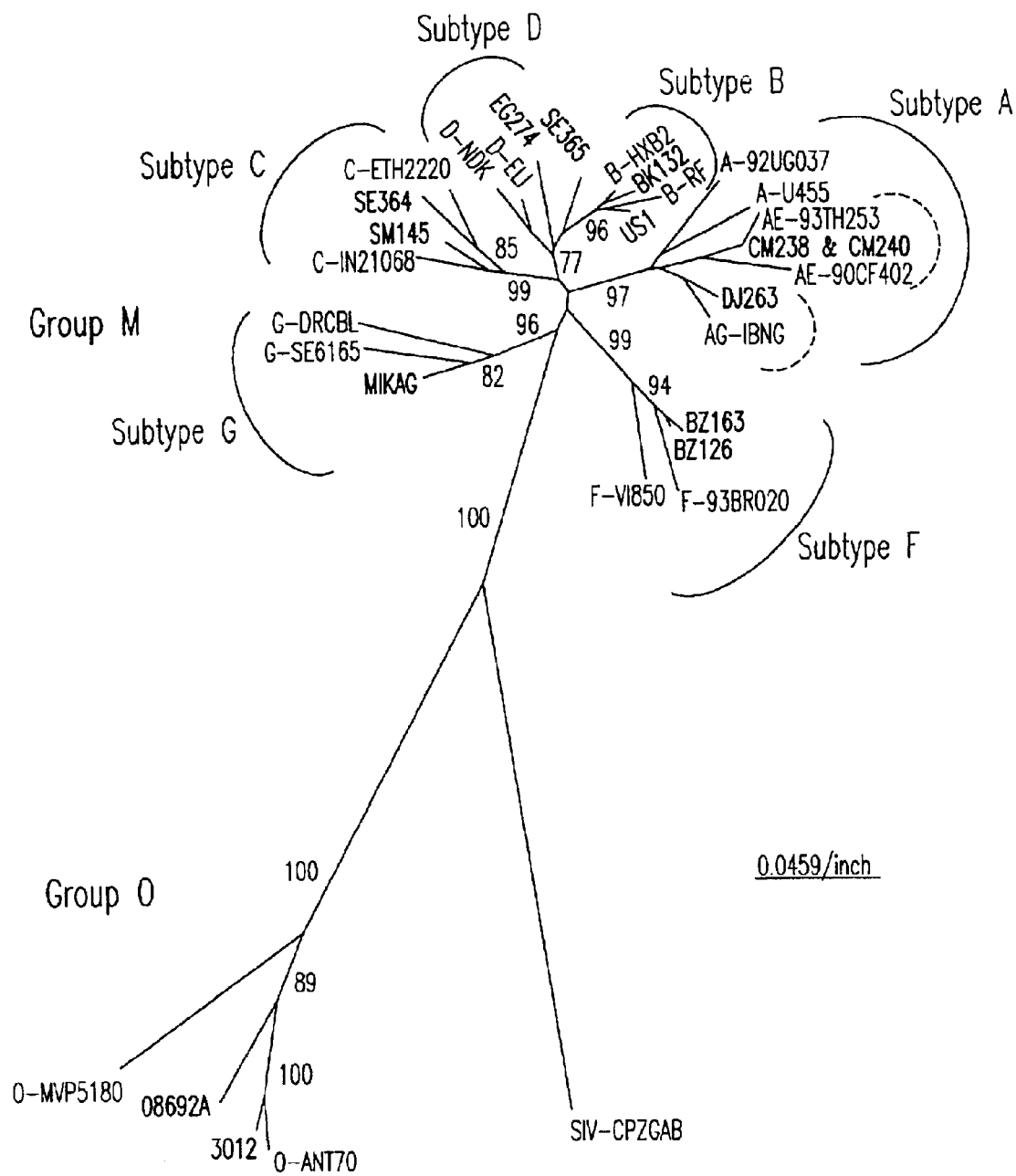
FIG. 1 illustrates the phylogenetic relationship of the viral isolates used for testing the primer sets to HIV-1 group M and group O reference strains based on analysis of the gag p24 gene (399 nucleotides). The viral isolates are denoted in bold. For the reference strains, the strain identifier is preceded by the subtype/group. Subtype groupings are indicated with an arc and subtype label; for CRF01_AE and CRF02_AG, the arc is dashed. Bootstrap values greater than 70% are shown at the major branch nodes.

The primer sets provided herein comprise two oligonucleotide primers that can be employed to amplify an HIV-1 target sequence in a test sample. The term "test sample" as used herein, means anything suspected of containing an HIV-1 target sequence. The test sample is, or can be derived from, any biological source, such as for example, blood, seminal fluid, ocular lens fluid, cerebral spinal fluid, milk, ascites fluid, synovial fluid, peritoneal fluid, amniotic fluid, tissue, fermentation broths, cell cultures and the like. The test sample can be used (i) directly as obtained from the source or (ii) following a pre-treatment to modify the character of the sample. Thus, the test sample can be pre-treated prior to use by, for example, preparing plasma from blood, disrupting cells or viral particles, preparing liquids from solid materials, diluting viscous fluids, filtering liquids, distilling liquids, concentrating liquids, inactivating interfering components, adding reagents, purifying nucleic acids, and the like.

A "target sequence" as used herein means a nucleic acid sequence that is amplified, detected, or both amplified and detected using the primer sets herein provided. Additionally, while the term target sequence is sometimes referred to as single stranded, those skilled in the art will recognize that the target sequence may actually be double stranded. Thus, in cases where the target is double stranded, primer sequences of the present invention will amplify both strands of the target sequence.

The primer sets that can be employed to amplify an HIV-1 target sequence preferably comprise deoxyribonucleic acid (DNA), or ribonucleic acid (RNA). Such primer sets can be employed according to any nucleic acid amplification technique that employs two oligonucleotides to amplify a target sequence. For example, the primer sets can be used in accordance with any of the well known nucleic acid amplification reactions such as, for example, NASBA or similar reactions such as TMA described in U.S. Pat. No. 5,399,491 (herein incorporated by reference); and PCR which is described in U.S. Pat. Nos. 4,683,195 and 4,683,202 (both of which are herein incorporated by reference). Additionally, in light of the RNA nature of the HIV-1 genome, the primer sets may be employed according to an "RT-PCR" format which is described in U.S. Pat. Nos. 5,322,770 and 5,310,652 both of which are herein incorporated by reference. Briefly, the RT-PCR format provides a method of transcribing a strand of DNA from an RNA target sequence. The copied DNA strand transcribed from the RNA target is commonly referred to as "cDNA" which then can serve as a template for amplification by any of the methods mentioned above. The process of generating cDNA shares many of the hybridization and extension principles surrounding other amplification methods such as PCR, but the enzyme employed should have reverse transcriptase activity. Enzymes having reverse transcriptase activity, as well as the RT-PCR process, are well known and therefore don't warrant further discussion. Additionally, other methods for synthesizing cDNA are also known and include commonly owned U.S. patent application Ser. No. 08/356,287 filed Feb. 22, 1995, which is herein incorporated by reference. Generally, therefore, amplifying an HIV-1 target sequence in a test sample will generally comprise the steps of contacting a test sample with a primer set and amplification reagents to form a reaction mixture and placing the reaction mixture under amplification conditions to thereby amplify the target sequence.

The phrase "amplification reaction reagents" as used herein means reagents which are well known for their use in nucleic acid amplification reactions and may include but are not limited to: a single or multiple reagent, reagents, enzyme or enzymes separately or individually having reverse transcriptase and/or polymerase activity or exonuclease activity; enzyme cofactors such as magnesium or manganese; salts; nicotinamide adenine dinucleotide (NAD); and deoxynucleoside triphosphates (dNTPs) such as, for example, deoxyadenosine triphosphate, deoxyguanosine triphosphate, deoxycytodine triphosphate and thymidine triphosphate. The exact amplification reagents employed are largely a matter of choice for one skilled in the art based upon the particular amplification reaction employed.

"Amplification conditions" are generally defined as conditions that promote annealing and extension of primer sequences and are well known and a matter of choice for those skilled in the art based upon the amplification reaction chosen. Thus, for example, in the case of PCR amplification conditions may comprise cycling the reaction mixture between two or more temperatures variously referred to as thermal cycling. Typically, PCR reactions are cycled between 20 to 50 times to achieve the desired amplification. In cases where so-called "isothermal" amplification reactions are employed, amplification occurs without cycling between different temperatures and an amplification product is produced as a result of forming a reaction mixture, although an initial temperature elevation may be required to initiate the reaction.

Primer sets which can be employed to amplify HIV-1 target sequences are presented in Table 1, Table 3, and Table 7, below (forward primers are shown as the top member of the pair, with the reverse primer being the bottom member of the pair). Most of these primer sets have been found to amplify an HIV-1 target sequence in a sensitive manner such that an amplification product produced using these primers can be detected on gel or using other means explained in detail below. The primer sets listed in Table 1, Table 3, and Table 7 preferably are sufficiently sensitive to produce a detectable amplification product from 100,000 copies of HIV-1 nucleic acid per milliliter of sample, more preferably from 10,000 copies of HIV-1 nucleic acid per milliliter of sample, and most preferably from 1,500 copies of HIV-1 nucleic acid per milliliter of sample.

TABLE 1

| Primer Set | Sequence (5'–3') | SEQ. ID. NO. |
|---|---|---|
| 1 | CCAGGAATATGGCAATTAGATTG | 1 |
|   | CCTGCCATCTGTTTTCCATA | 2 |
| 2 | GCAGTCCATGTAGCCAGTGG | 3 |
|   | CCTGCCATCTGTTTTCCATA | 2 |
| 3 | CACAATTTTAAAAGAAAAGGGGGGATTGG | 4 |
|   | CCTGCCATCTGTTTTCCATA | 2 |

TABLE 1-continued

| Primer Set | Sequence (5'–3') | SEQ. ID. NO. |
|---|---|---|
| 4 | TAGACATAATAGCAACAGACATACAAAC | 5 |
|  | CCTGCCATCTGTTTTCCATA | 2 |
| 5 | TATTACAGGGACAGCAGAGA | 6 |
|  | CCTGCCATCTGTTTTCCATA | 2 |
| 6 | GACAGCAGAGACCCAATTTGGAAAGGACC | 7 |
|  | CCTGCCATCTGTTTTCCATA | 2 |
| 7 | TGGAAAGGTGAAGGGGCAGTAGT | 8 |
|  | CCTGCCATCTGTTTTCCATA | 2 |
| 8 | AATTGGAGAGCAATGGCTAGTGA | 9 |
|  | CCTTCTAAATGTGTACAATC | 10 |
| 9 | AATTGGAGAGCAATGGCTAGTGA | 9 |
|  | TCTGCTGGGATAACTTCTGCTTCTA | 11 |
| 10 | CCAGGAATATGGCAATTAGATTG | 1 |
|  | TTATTCATAGATTCTACTACTCCTTGACTTTG | 12 |
| 11 | AAGGCAGCCTGTTGGTGG | 13 |
|  | GTTTGTATGTCTGTTGCTATTATGTCTA | 14 |
| 12 | AAGGCAGCCTGTTGGTGG | 13 |
|  | ACTACTGCCCCTTCACCTTTCCA | 15 |
| 13 | AAGGCAGCCTGTTGGTGG | 13 |
|  | CCTGCCATCTGTTTTCCATA | 2 |
| 14 | AATTGGAGAGCAATGGCTAGTGA | 9 |
|  | TTATTCATAGATTCTACTACTCCTTGACTTTG | 12 |
| 15 | CCAGGAATATGGCAATTAGATTG | 1 |
|  | TCTGCTGGGATAACTTCTGCTTCTA | 11 |
| 16 | GATTGTACACATTTAGAAGG | 16 |
|  | TTATTCATAGATTCTACTACTCCTTGACTTTG | 12 |
| 17 | GATTGTACACATTTAGAAGG | 16 |
|  | AATACTGCCATTTGTACTGCTGT | 17 |
| 18 | GCAGTCCATGTAGCCAGTGG | 3 |
|  | TTATTCATAGATTCTACTACTCCTTGACTTTG | 12 |
| 19 | GCAGTCCATGTAGCCAGTGG | 3 |
|  | CCCCCAATCCCCCCTTTTCTTTTAAAATTGTG | 18 |
| 20 | AAGATGGCCAGTAAAAGTAATACACACAGACAA | 19 |
|  | CCCCCAATCCCCCCTTTTCTTTTAAAATTGTG | 18 |
| 21 | AAGGCAGCCTGTTGGTGG | 13 |
|  | AATACTGCCATTTGTACTGCTGT | 17 |
| 22 | AAGGCAGCCTGTTGGTGG | 13 |
|  | ACCCGAAAATTTTGAATTTTT | 20 |
| 23 | CAAAGTCAAGGAGTAGTAGAATCTATGAATAA | 21 |
|  | CCCCCAATCCCCCCTTTTCTTTTAAAATTGTG | 18 |
| 24 | CAAAGTCAAGGAGTAGTAGAATCTATGAATAA | 21 |
|  | GTTTGTATGTCTGTTGCTATTATGTCTA | 14 |
| 25 | CAAAGTCAAGGAGTAGTAGAATCTATGAATAA | 21 |
|  | ACCCGAAAATTTTGAATTTTT | 20 |
| 26 | CACAATTTTAAAAGAAAAGGGGGATTGG | 4 |
|  | ACCCGAAAATTTTGAATTTTT | 20 |
| 27 | TAGACATAATAGCAACAGACATACAAAC | 5 |
|  | ACTACTGCCCCTTCACCTTTCCA | 15 |
| 28 | CAAAGTCAAGGAGTAGTAGAATCTATGAATAA | 21 |
|  | TCTCTGCTGTCCCTGTAATA | 22 |
| 29 | CAAAGTCAAGGAGTAGTAGAATCTATGAATAA | 21 |
|  | GGTCCTTTCCAAATTGGGTCTCTGCTGTC | 23 |
| 30 | TAGACATAATAGCAACAGACATACAAAC | 5 |
|  | GGTCCTTTCCAAATTGGGTCTCTGCTGTC | 23 |

Amplification products produced using the primer sets provided herein may be detected using a variety of detection technologies well known in the art. For example, amplification products may be detected using agarose gel electrophoresis and visualization by ethidium bromide staining and exposure to Ultraviolet (UV) light or by sequence analysis of the amplification product for confirmation of HIV-1 identity.

Alternatively, amplification products may be detected by oligonucleotide hybridization with a probe. Probe sequences generally are 10 to 50 nucleotides long, more typically 15 to 40 nucleotides long, and similarly to primer sequences, probe sequences are also nucleic acid. Hence, probes may comprise DNA, RNA or nucleic acid analogs such as uncharged nucleic acid analogs including but not limited to peptide nucleic acids (PNAs) which are disclosed in International Patent Application WO 92/20702 or morpholino analogs which are described in U.S. Pat. Nos. 5,185,444, 5,034,506, and 5,142,047 all of which are herein incorporated by reference. Such sequences can routinely be synthesized using a variety of techniques currently available. For example, a sequence of DNA can be synthesized using conventional nucleotide phosphoramidite chemistry and the instruments available from Applied Biosystems, Inc, (Foster City, Calif.); DuPont, (Wilmington, Del.); or Milligen, (Bedford, Mass.). Similarly, and when desirable, probes can be labeled using methodologies well known in the art such as described in U.S. Pat. Nos. 5,464,746; 5,424,414; and 4,948,882 all of which are herein incorporated by reference. Additionally, probes typically hybridize with the target sequence between the primer sequences. In other words, the probe sequence typically is not coextensive with either primer.

The term "label" as used herein means a molecule or moiety having a property or characteristic which is capable of detection. A label can be directly detectable, as with, for example, radioisotopes, fluorophores, chemiluminophores, enzymes, colloidal particles, fluorescent microparticles and the like; or a label may be indirectly detectable, as with, for example, specific binding members. It will be understood that directly detectable labels may require additional components such as, for example, substrates, triggering reagents, light, and the like to enable detection of the label. When indirectly detectable labels are used, they are typically used in combination with a "conjugate". A conjugate is typically a specific binding member which has been attached or coupled to a directly detectable label. Coupling chemistries for synthesizing a conjugate are well known in the art and can include, for example, any chemical means and/or physical means that does not destroy the specific binding property of the specific binding member or the detectable property of the label. As used herein, "specific binding member" means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; enzyme cofactors or substrates and enzymes; and the like.

Probe sequences can be employed using a variety of homogeneous or heterogeneous methodologies to detect amplification products. Generally all such methods employ a step where the probe hybridizes to a strand of an amplification product to form an amplification product/probe hybrid. The hybrid can then be detected using labels on the primer, probe or both the primer and probe. Examples of homogeneous detection platforms for detecting amplification products include the use of FRET (fluorescence resonance energy transfer) labels attached to probes that emit a signal in the presence of the target sequence. So-called TaqMan assays described in U.S. Pat. No. 5,210,015 (herein incorporated by reference) and Molecular Beacon assays described in U.S. Pat. No. 5,925,517 (herein incorporated by reference) are examples of techniques that can be employed to homogeneously detect nucleic acid sequences. According to homogenous detection techniques, products of the amplification reaction can be detected as they are formed or in a so-called real time manner. As a result, amplification product/probe hybrids are formed and detected while the reaction mixture is under amplification conditions.

Heterogeneous detection formats typically employ a capture reagent to separate amplified sequences from other materials employed in the reaction. Capture reagents typically are a solid support material that is coated with one or more specific binding members specific for the same or different binding members. A "solid support material", as used herein, refers to any material which is insoluble, or can be made insoluble by a subsequent reaction. Solid support materials thus can be a latex, plastic, derivatized plastic, magnetic or non-magnetic metal, glass or silicon surface or surfaces of test tubes, microtiter wells, sheets, beads, microparticles, chips, and other configurations known to those of ordinary skill in the art. To facilitate detection of an amplification product/probe hybrid in a heterogeneous type manner, the probes can be labeled with a first binding member which is specific for its binding partner which is attached to a solid support material such as a microparticle. Similarly, primers may be labeled with a second binding member specific for a conjugate as defined above. The amplification products bound to the probes can then be separated from the remaining reaction mixture by contacting the reaction mixture with the above solid support and then removing the solid support from the reaction mixture. Any amplification product/probe hybrids bound to the solid support may then be contacted with a conjugate to detect the presence of the hybrids on the solid support.

Whether detected in a homogeneous or heterogeneous manner, methods for detecting a target sequence in a test sample will generally comprise the steps of contacting a test sample with a primer set provided herein, and amplification reagents to form a reaction mixture. The reaction mixture then is placed under amplification conditions to form an amplification product, as specified above. The amplification product is then detected as an indication of the presence of the target sequence in the test sample. As stated above, the reaction product may be detected using gel electrophoresis, heterogeneous methods or homogeneous methods. Accordingly, the reaction product may be detected in the reaction mixture while it is under amplification conditions with homogeneous techniques such as with TaqMan Probes or Molecular Beacons. Alternatively, the amplification product may be detected after amplification of the target sequence is complete using heterogeneous techniques or gels.

The present invention also provides oligonucleotide sets useful for amplifying and detecting an HIV-1 target sequence in a test sample. These oligonucleotide sets, or "oligo sets", comprise a primer set and a molecular beacon probe that can be used in the manner set forth above. Additionally, the oligo sets may be packaged in suitable containers and provided with additional reagents such as, for example, amplification reagents (also in suitable containers) to provide kits for detecting HIV-1 in a test sample.

In the case of detection using molecular beacons, probe sequences are modified and labeled with a fluorescent detection label and a fluorescence-quenching group. The probe portion of the sequence is used to hybridize with the sequence generated by the primer sequence, and typically hybridizes with a sequence that does not include the primer sequence. In this format, it is also possible to probe with multiple beacons, each labeled with a different fluorophore. Upon formation of the copy sequence/molecular beacon hybrids, the differential labels from different molecular beacons can be used to separate and detect slight sequence variations that may be expected among the amplified products. Examples of circumstances in which variations in amplified sequences might be expected include use of multiple primer sets in the amplification reaction (e.g. HIV-1-specific and HIV-2-specific), addition and co-amplification of an internal control sequence to the initial target sequence, or the potential for a single set of primers to amplify multiple HIV subtypes, as these primer sets are designed to do, which then might be distinguished by subtype specific molecular beacon sequences. Detection is performed on any of a variety of instrumentation available for fluorescence detection as is well known by those skilled in the art.

The following examples are provided to further illustrate the present invention and not intended to limit the invention.

EXAMPLES

The following examples demonstrate amplification and detection of various subtypes of HIV-1 using the primer sets herein provided. These DNA sequences comprising the primer sets are identified as SEQUENCE ID NO. 1, SEQUENCE ID NO. 2, SEQUENCE ID NO. 3, SEQUENCE ID NO. 4, SEQUENCE ID NO. 5, SEQUENCE ID NO. 6, SEQUENCE ID NO. 7, SEQUENCE ID NO. 8, SEQUENCE ID NO. 9, SEQUENCE ID NO. 10, SEQUENCE ID NO. 11, SEQUENCE ID NO. 12, SEQUENCE ID NO. 13, SEQUENCE ID NO. 14, SEQUENCE ID NO. 15, SEQUENCE ID NO. 16, SEQUENCE ID NO. 17, SEQUENCE ID NO. 18, SEQUENCE ID NO. 19, SEQUENCE ID NO. 20, SEQUENCE ID NO. 21, SEQUENCE ID NO. 22, SEQUENCE ID NO. 23, SEQUENCE ID NO. 24, SEQUENCE ID NO. 25, SEQUENCE ID NO. 26, SEQUENCE ID NO. 27, SEQUENCE ID NO. 28, SEQUENCE ID NO. 29, SEQUENCE ID NO. 30, SEQUENCE ID NO. 31, SEQUENCE ID NO. 32, SEQUENCE ID NO. 33, SEQUENCE ID NO. 34, SEQUENCE ID NO. 35, SEQUENCE ID NO. 37, SEQUENCE ID NO. 38, and SEQUENCE ID NO. 40.

The probe sequences employed in the examples are identified as: SEQUENCE ID NO. 41, SEQUENCE ID NO. 42, SEQUENCE ID NO. 43, SEQUENCE ID NO. 44, SEQUENCE ID NO. 45, SEQUENCE ID NO. 46, SEQUENCE ID NO. 47, SEQUENCE ID NO. 48, SEQUENCE ID NO. 49, SEQUENCE ID NO. 50, SEQUENCE ID NO. 51, SEQUENCE ID NO. 52, SEQUENCE ID NO. 53, SEQUENCE ID NO. 54, SEQUENCE ID NO. 55, SEQUENCE ID NO. 56, SEQUENCE ID NO. 57, SEQUENCE ID NO. 58, SEQUENCE ID NO. 59, SEQUENCE ID NO. 60, SEQUENCE ID NO. 61, SEQUENCE ID NO. 62, SEQUENCE ID NO. 63, SEQUENCE ID NO. 64 and SEQUENCE ID NO. 65.

Example 1

Preparation of Oligonucleotide Primers

Oligonucleotide primers were designed to amplify all known HIV-1 group M strains, HIV-1 group O strains, or HIV-1 group M and group O strains, by RT-PCR. These primers were SEQUENCE ID NO. 1, SEQUENCE ID NO. 2, SEQUENCE ID NO. 3, SEQUENCE ID NO. 4, SEQUENCE ID NO. 5, SEQUENCE ID NO. 6, SEQUENCE ID NO. 7, SEQUENCE ID NO. 8, SEQUENCE ID NO. 9, SEQUENCE ID NO. 10, SEQUENCE ID NO. 11, SEQUENCE ID NO. 12, SEQUENCE ID NO. 13, SEQUENCE ID NO. 14, SEQUENCE ID NO. 15, SEQUENCE ID NO. 16, SEQUENCE ID NO. 17, SEQUENCE ID NO. 18, SEQUENCE ID NO. 19, SEQUENCE ID NO. 20, SEQUENCE ID NO. 21, SEQUENCE ID NO. 22, and SEQUENCE ID NO. 23, SEQUENCE ID NO. 24, SEQUENCE ID NO. 25, SEQUENCE ID NO. 26, SEQUENCE ID NO. 27, SEQUENCE ID NO. 28, SEQUENCE ID NO. 29, SEQUENCE ID NO. 30, SEQUENCE ID NO. 31, SEQUENCE ID NO. 32, SEQUENCE ID NO. 33, SEQUENCE ID NO. 34, SEQUENCE ID NO. 35, SEQUENCE ID NO. 37, SEQUENCE ID NO. 38, SEQUENCE ID NO. 40. Primer sequences were synthesized using standard oligonucleotide synthesis methodology.

Example 2

Isolate Characterization

To determine whether the oligonucleotide primer sets of this invention (Table 1) could detect and amplify HIV-1 variant strains, a panel of group M (including the most prevalent subtypes), CRF, and group O viral isolates was used to examine performance. The HIV-1 isolates were obtained from several sources. Twelve group M isolates were obtained from the Walter Reed Army Institute of Research (WRAIR, Bethesda, Md.); one group O isolate was obtained through a Collaborative Research and Development Agreement with the Centers for Disease Control and Prevention (Atlanta, Ga.); and one group O isolate was received from Serologicals, Inc. (Atlanta, Ga.). Cell-free virus stocks from the isolates were prepared by SRA Technologies (Rockville, Md.). The viral isolates were characterized by sequence and phylogenetic analysis to designate HIV-1 group/subtype classification.

Figure 2:
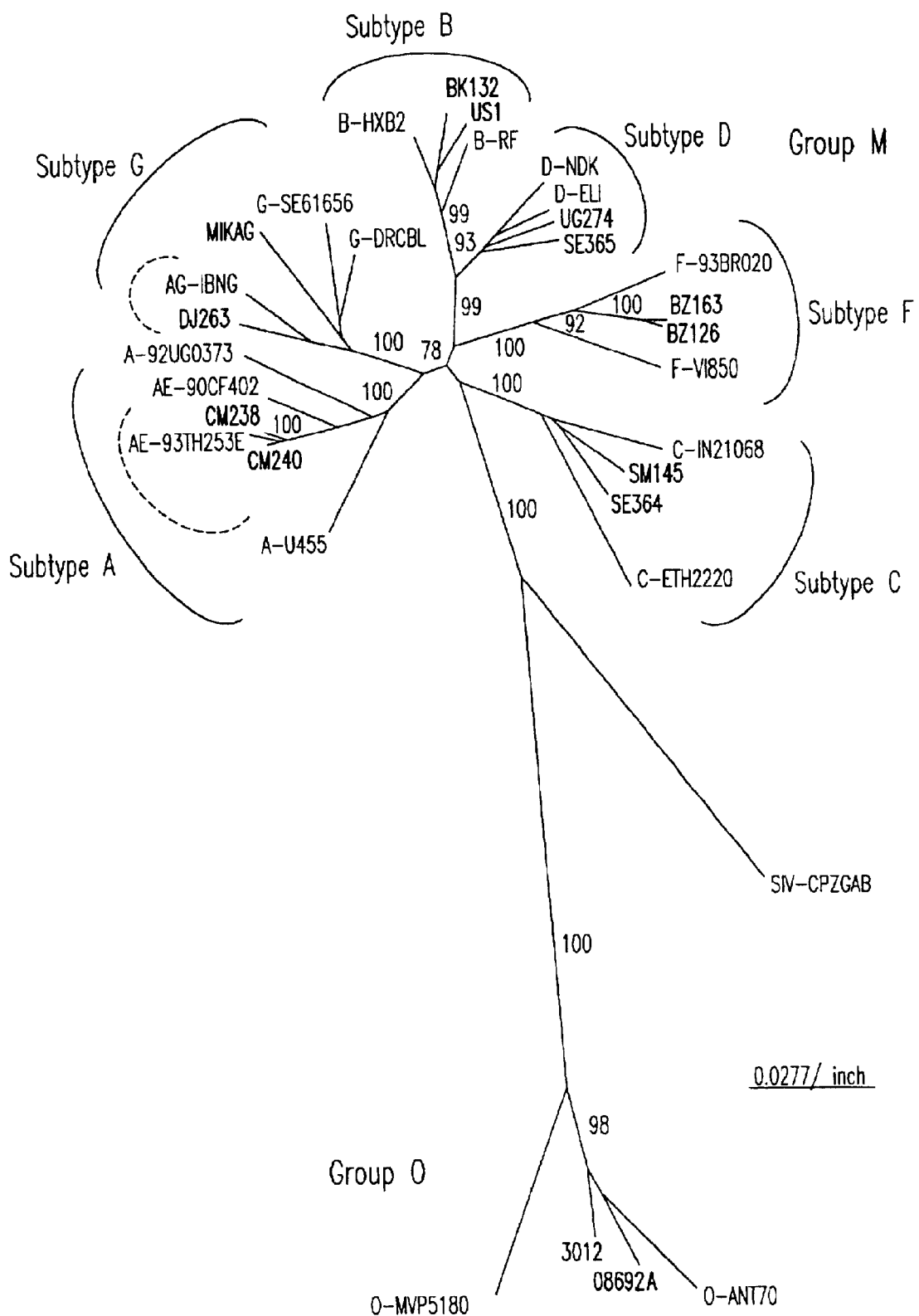
FIG. 2 depicts the phylogenetic relationship of the viral isolates used for testing the primer sets to HIV-1 group M and group O reference strains based on analysis of the pol integrase gene (864 nucleotides). The viral isolates are denoted in bold. For the reference strains, the strain identifier is preceded by the subtype/group. Subtype groupings are indicated with an arc and subtype label; for CRF01_AE and CRF02_AG, the arc is dashed. Bootstrap values of 70% or more are shown at the major branch nodes.
Figure 3:
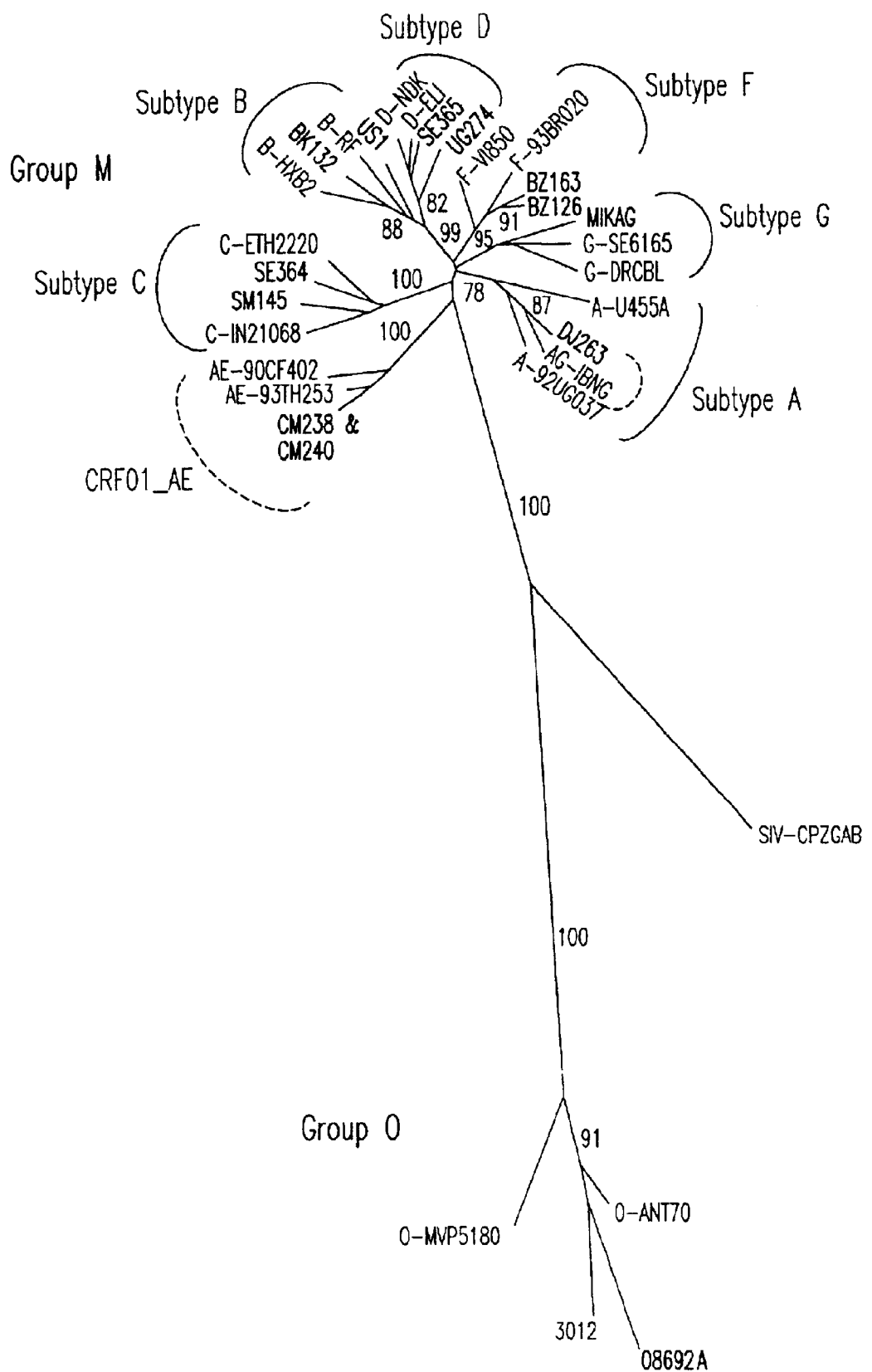
FIG. 3 illustrates the phylogenetic relationship of the viral isolates used for testing the primer sets to HIV-1 group M and group O reference strains based on analysis of the env gp41 immunodominant region (369 nucleotides). The viral isolates are denoted in bold. For the reference strains, the strain identifier is preceded by the subtype/group. Subtype groupings are indicated with an arc and subtype label; for CRF01_AE and CRF02_AG, the arc is indicated by a broken line. Bootstrap values greater than 70% are shown at the major branch nodes.

Three regions of the HIV-1 genome were targeted for sequence analysis: gag p24 (399 nucleotides), pol integrase (864 nucleotides), and env gp41 immunodominant region (IDR; 369 nucleotides). Virus stocks were diluted into HIV-1-seronegative human plasma. Total nucleic acid was extracted from 200–400 μl plasma using the QIAamp Blood Kit (Qiagen Inc., Valencia, Calif.). Primers and conditions for RT-PCR amplification of all three regions have been described previously (Brennan et. al., AIDS 11: 1823–1832 (1997); Brennan et. al., AIDS Res. Hum. Retroviruses 13:901–904 (1997); Hackett et. al., AIDS Res. Hum. Retroviruses 13:1155–1158 (1997); Swanson et. al., J. Virol. Methods 89:97–108 (2000)). Amplification products were purified using a QIAquick PCR Purification Kit (Qiagen Inc.). Both strands of the purified PCR products were sequenced directly using an ABI model 377 automated sequencer (PE Applied Biosystems, Foster City, Calif.) and the ABI Prism Big Dye Terminator Cycle Sequencing Kit (PE Applied Biosystems). Nucleotide sequences were aligned to those from established reference strains, representing all group M subtypes and group O, and analyzed using Lasergene 99 (DNASTAR, Inc., Madison, Wis.). The Phylip software package (version 3.5c, J. Felsenstein, University of Washington, Seattle, Wash.) was used for phylogenetic analysis. Evolutionary distances were estimated using DNADIST (Kimura two-parameter method) and phylogenetic reconstruction by the neighbor-joining method (NEIGHBOR). Reproducibility of branching patterns was examined by bootstrap analysis (100 samplings) with SEQBOOT. All three regions were successfully RT PCR-amplified and sequenced from all fourteen viral isolates. Results of the phylogenetic analysis are shown in FIGS. 1–3 and summarized in Table 2.

TABLE 2

| HIV-1 Isolate | Subtype | gag | pol | env | Country |
|---|---|---|---|---|---|
| Group M: | | | | | |
| BK132 | B | B | B | B | Thailand |
| US1 | | B | B | B | United States |
| SE364 | C | C | C | C | Senegal |
| SM145 | | C | C | C | Somalia |
| SE365 | D | D | D | D | Senegal |
| UG274 | | D | D | D | Uganda |
| CM238 | CRF01_AE | A | A | E | Thailand |
| CM240 | | A | A | E | Thailand |
| BZ126 | F | F | F | F | Brazil |
| BZ163 | | F | F | F | Brazil |
| MIKAG* | G | G | G | G | Kenya |
| DJ263 | CRF02_AG (IbNG) | A | G | A | Djibouti |
| Group O: | | | | | |
| 08692A | | | | | United States |
| 3012 | | | | | Spain |

*MIKAG is the sample ID used internally for the isolate typically identified as HH8793 (Carr, J. K. et. al., Virology 247:22–31 (1998)).

The panel of isolates chosen for testing represents a wide geographic range and includes the most widely distributed subtypes of group M including two CRF strains and group O. These isolates were chosen based on the results from the phylogenetic analysis of the pol integrase gene since the primers of this invention are designed to target the pol integrase gene of HIV-1. Of the 14 isolates, there is an even distribution of two per group M subtype, as indicated by the analysis of the pol integrase region (FIG. 2, Table 2), and two group O isolates. As described previously the CRF01_AE is subtype A in the pol integrase region, and therefore, detection of the subtype CRF01_AE isolates demonstrates the ability of the primer sets to detect both subtypes A and CRF01_AE. Testing of this panel provides evidence that the primers of this invention are effective for the detection of the genetically diverse strains of HIV-1.

Example 3

HIV-1 Subtype Detection

The viral isolates characterized in Example 2 were used for testing the primer sets of Table 1 to demonstrate that the primer sets will detect each of the HIV-1 group M subtypes and CRF strains, as well as group O isolates.

To facilitate analysis of the PCR amplification products, dilutions of the purified HIV-1 RNA were reverse transcribed, and the complete pol integrase gene was PCR amplified using the group M (polI8 and polI5) or group O (O-polI8 and O-polI5) specific primers listed in Table 3. A second round of amplification was then performed using the HIV-1 primer sets of the present invention (Table 1) in separate reactions.

TABLE 3

| Primer Set | Primer | Sequence 5'-3'* | Sequence ID NO |
|---|---|---|---|
| 46 | polI8 | TAGTGGGATGTGTACTTCTGAAC | 24 |
|  | polI5 | CACACAAAGGRATTGGAGGAAATG | 25 |
| 47 | O-polI8 | GATTYCTGGATTCATAATGATG | 26 |
|  | O-polI5 | GTATCTTACATGGGTTCCTGC | 27 |

*Degenerate nucleotide positions are identified using the IUPAC code.

RT-PCR was performed using the components of the Perkin Elmer Gene Amp RNA PCR kit according to the manufacturer's instructions. Complementary DNA (cDNA) was synthesized by reverse transcription of nucleic acid with sample volume of 3 µl in a total reaction volume of 20 µl, containing the following reagents: PCR Buffer II, 5 mM $MgCl_2$, MuLV Reverse Transcriptase at a concentration of 2.5 U/reaction, dNTPs (dATP, dGTP, dTTP and dCTP) at a concentration of 1.0 mM each, RNase inhibitor at a concentration of 1 U/reaction, and 1 µM of primer. Reaction mixtures were reverse transcribed and amplified in a Perkin-Elmer 9600 Thermal Cycler. RT reaction mixtures were first incubated at 42° C. for 40 minutes followed by 5 minutes at 99° C.

The first round of PCR amplification was carried out by adding additional reagents directly to the 20 µl cDNA reaction for a total reaction volume of 100 µl. Reactions contained final concentrations of 5 mM $MgCl_2$, 2.5 U/reaction of Amplitaq DNA polymerase and 0.5 µM each of the forward and reverse primers. The reactions were then cycled as follows: initial denaturation at 95° C. for 1 minute, 40 cycles of 94° C. for 30 seconds, 45° C. for 30 seconds, then 72° C. for 90 seconds, followed by a final incubation at 72° C. for 10 minutes.

The full-length pol integrase amplification products were then utilized as templates to examine the performance of the HIV-1 primer sets of the present invention (Table 1). Each primer set was tested individually in a 100 µl reaction containing: 5 µl of primary PCR reaction, PCR Buffer, dNTPs (dATP, dGTP, dTTP and dCTP) at a concentration of 0.2 mM each, 2.5 U/reaction of Amplitaq DNA polymerase and 0.5 µM of each primer. Reaction mixtures were amplified in a Perkin-Elmer 9600 or 9700 Thermal Cycler. The reaction mixtures were cycled as follows: initial denaturation at 95° C. for 1 minute, 40 cycles of 94° C. for 30 seconds, 50° C. or 55° C. for 30 seconds, then 72° C. for 90 seconds, followed by a final incubation at 72° C. for 10 minutes. Samples were held at 4° C. prior to agarose gel electrophoresis.

Figure 4:
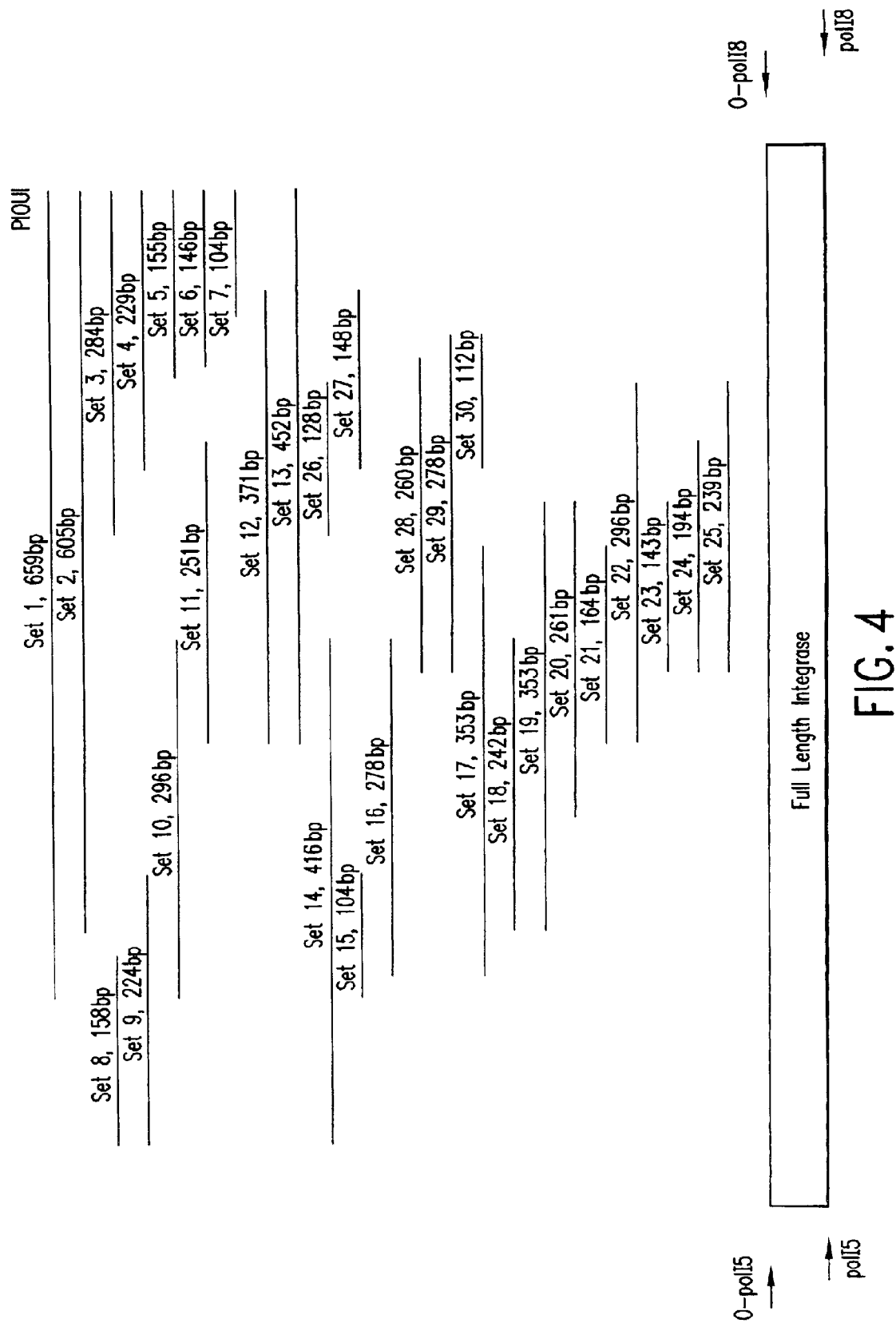
FIG. 4 illustrates a schematic of the expected PCR amplification fragments from each primer set aligned with the full length pol integrase gene. Each fragment is labeled with the primer set number and the expected fragment length in base pairs (bp). Also shown are the relative position and direction of the primers of Table 3 used for the first round amplification of the full length pct integrase gene for both group M and O isolates.
Figure 5A:
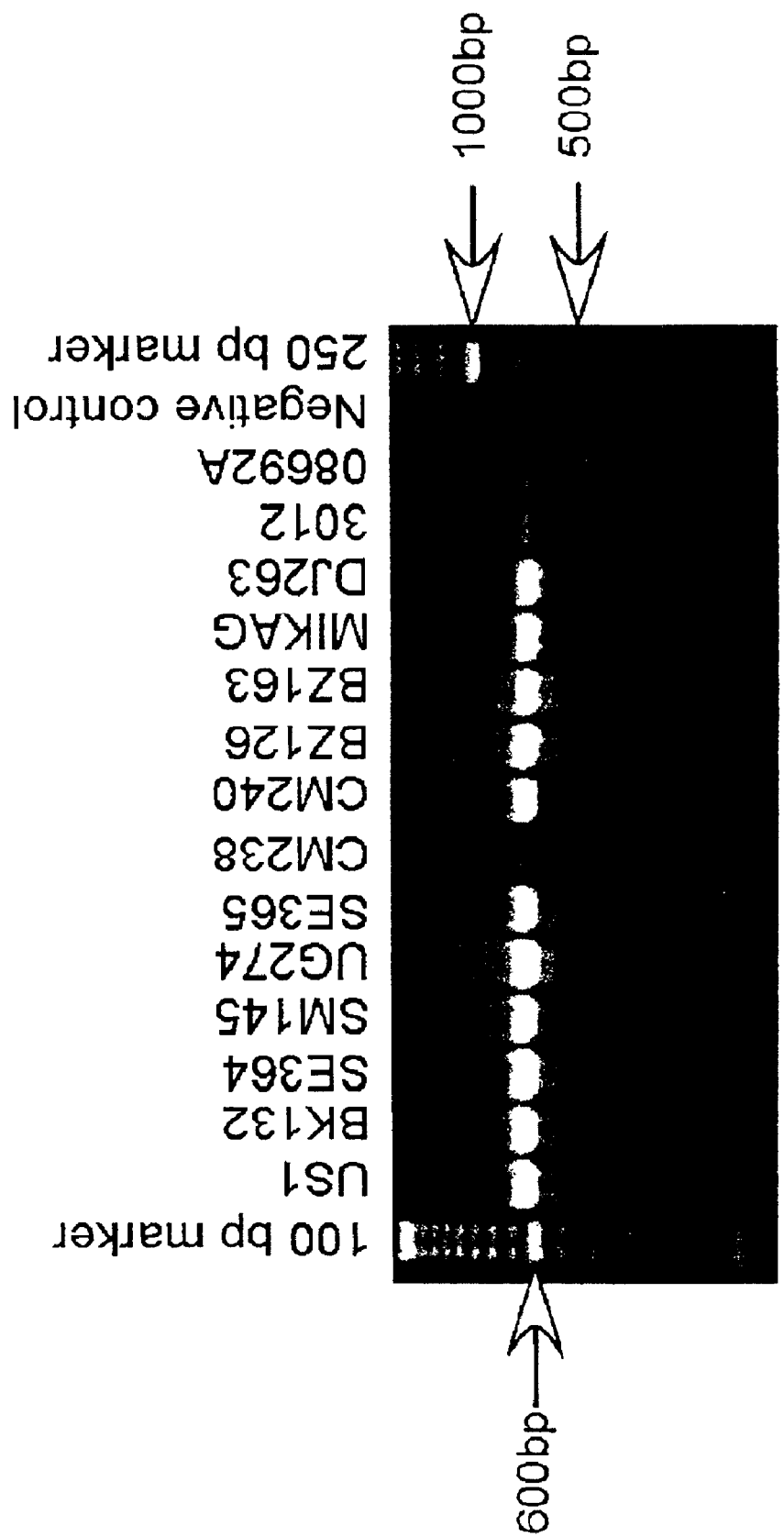
FIGS. 5A–D shows detection of RT PCR-amplified pol integrase fragments by agarose gel electrophoresis and ethidium bromide staining for all test isolates.
Figure 5B:
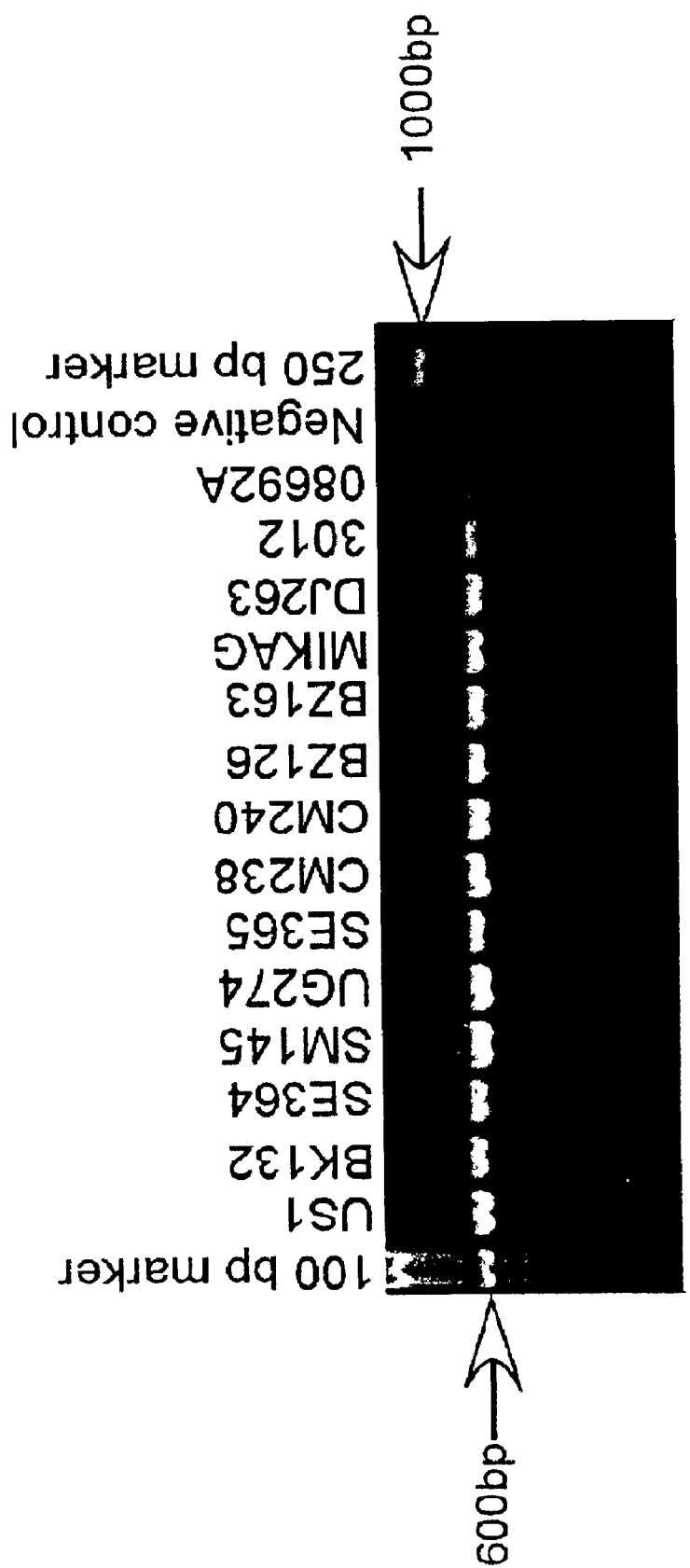
Figure 5C:
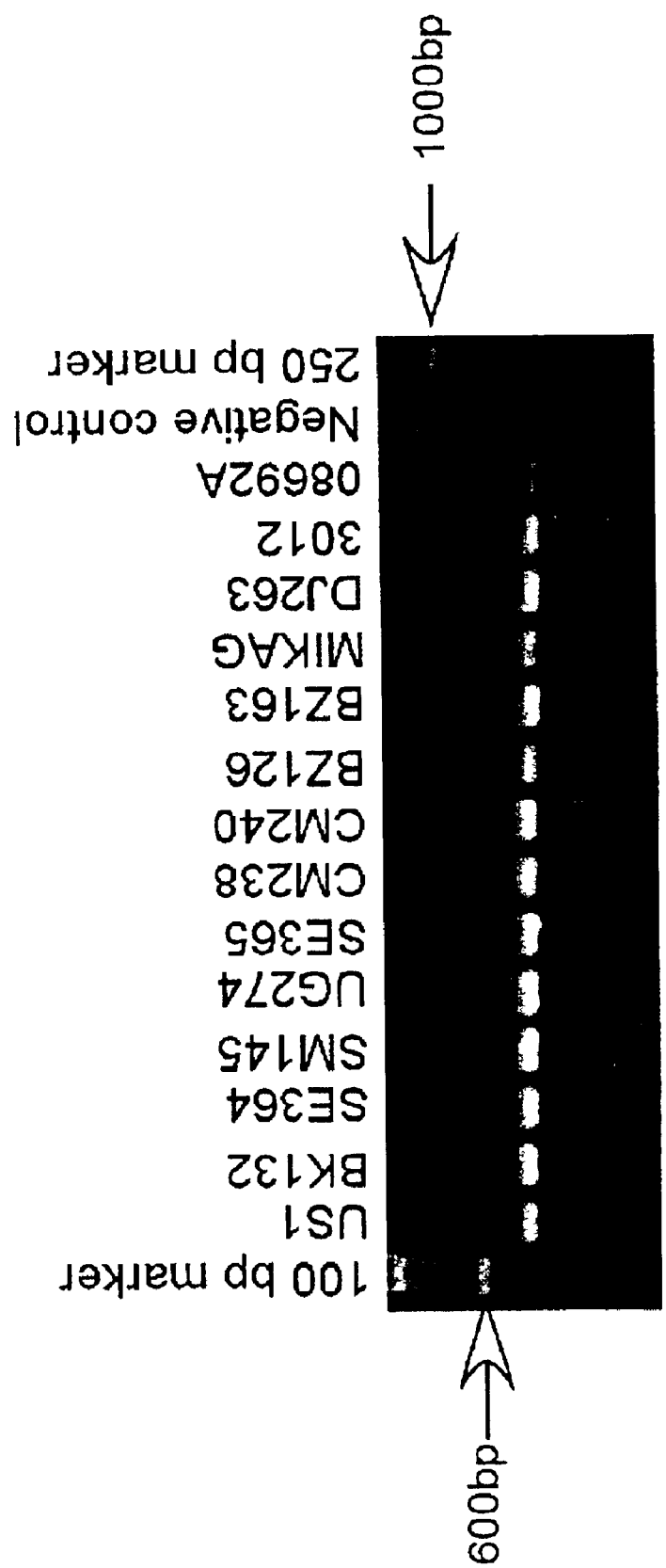
Figure 5D:
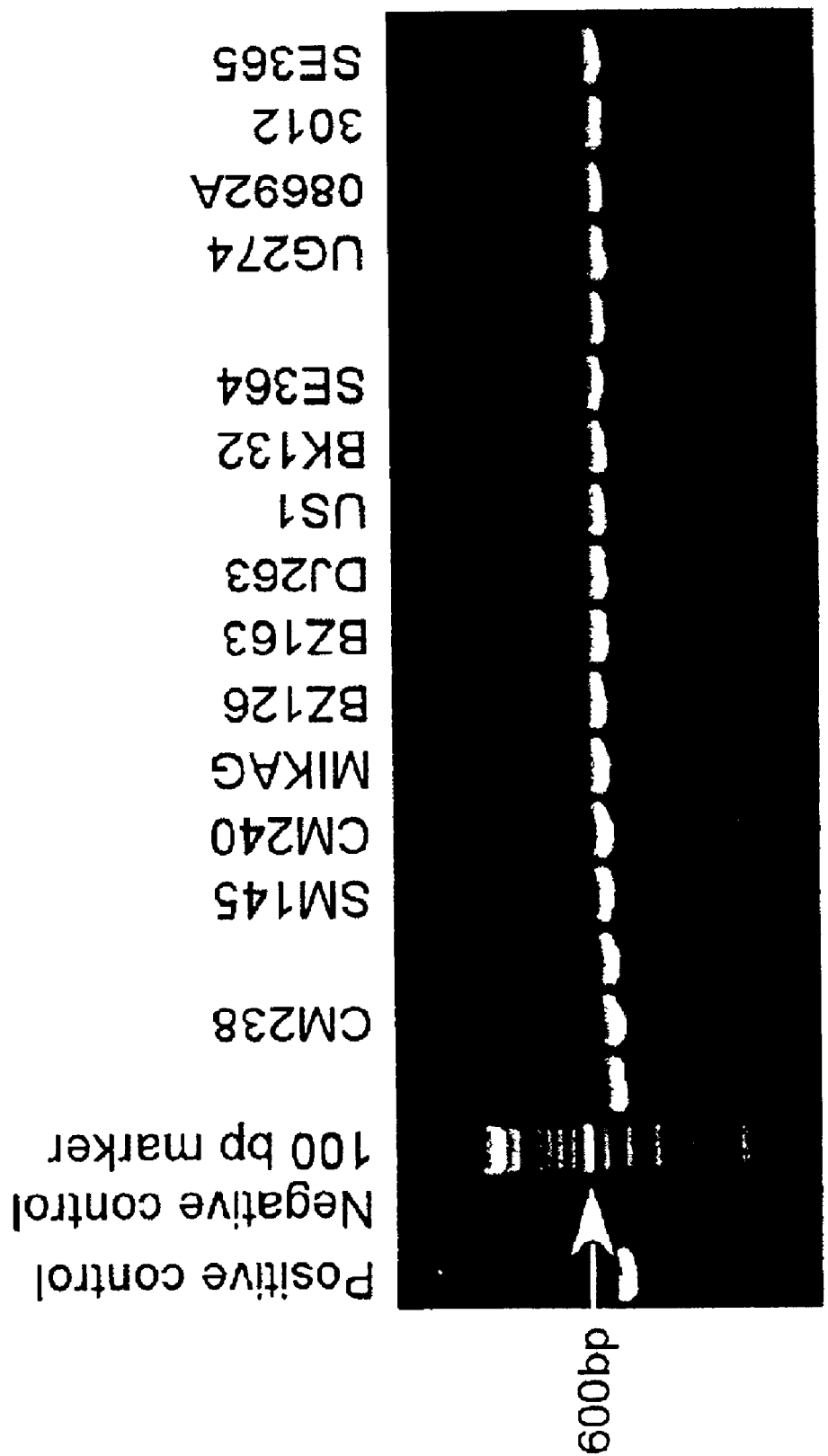
Figure 6:
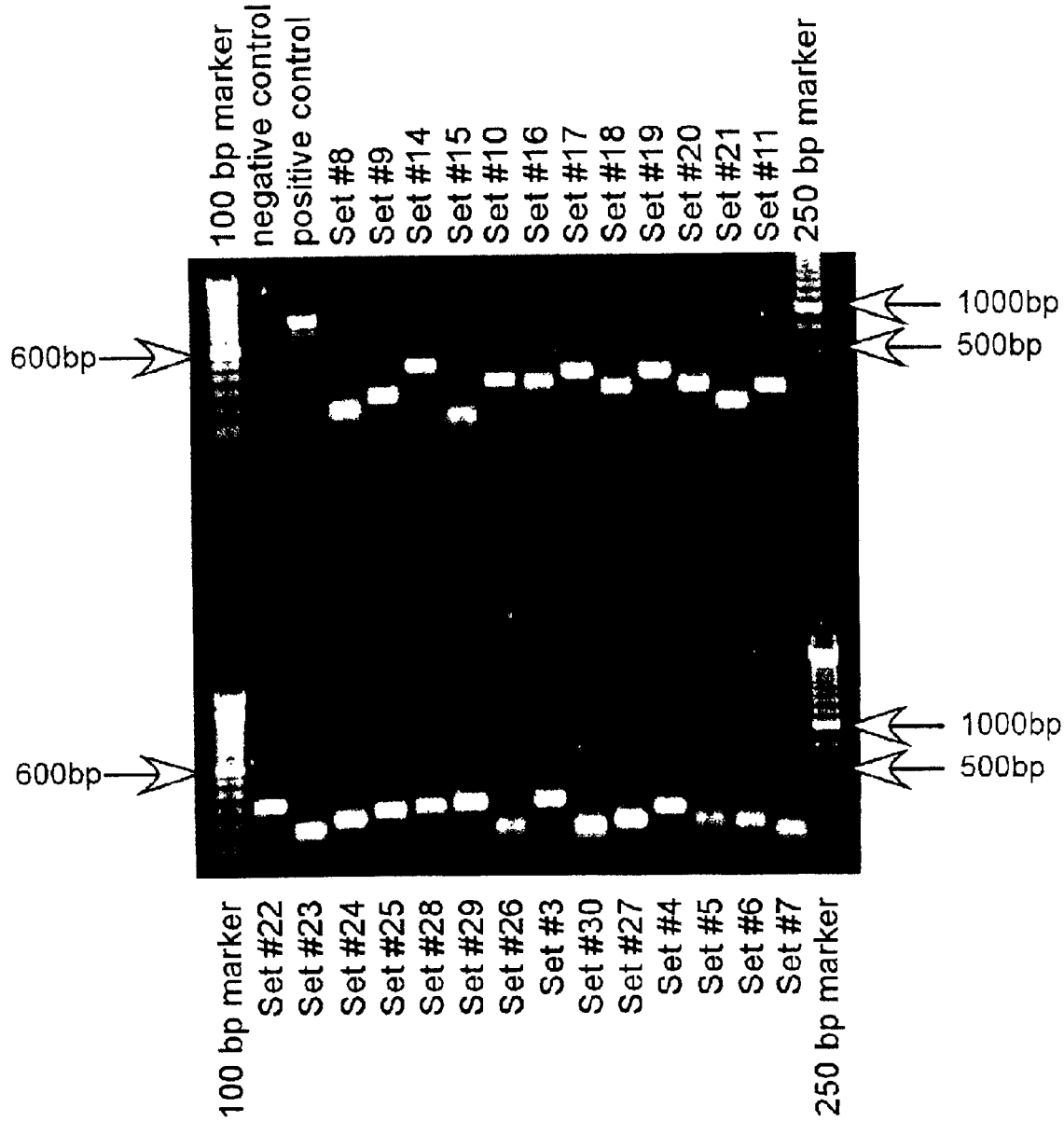
FIG. 6 shows detection by agarose gel electrophoresis and ethidium bromide staining of RT PCR-amplified group M subtype CRF02_AG, isolate DJ263 pol integrase fragments using all primer sets not shown in FIGS. 5–8. Molecular weight bands corresponding to 600, 500 and 1000 bp markers are highlighted with arrows.
Figure 7A:
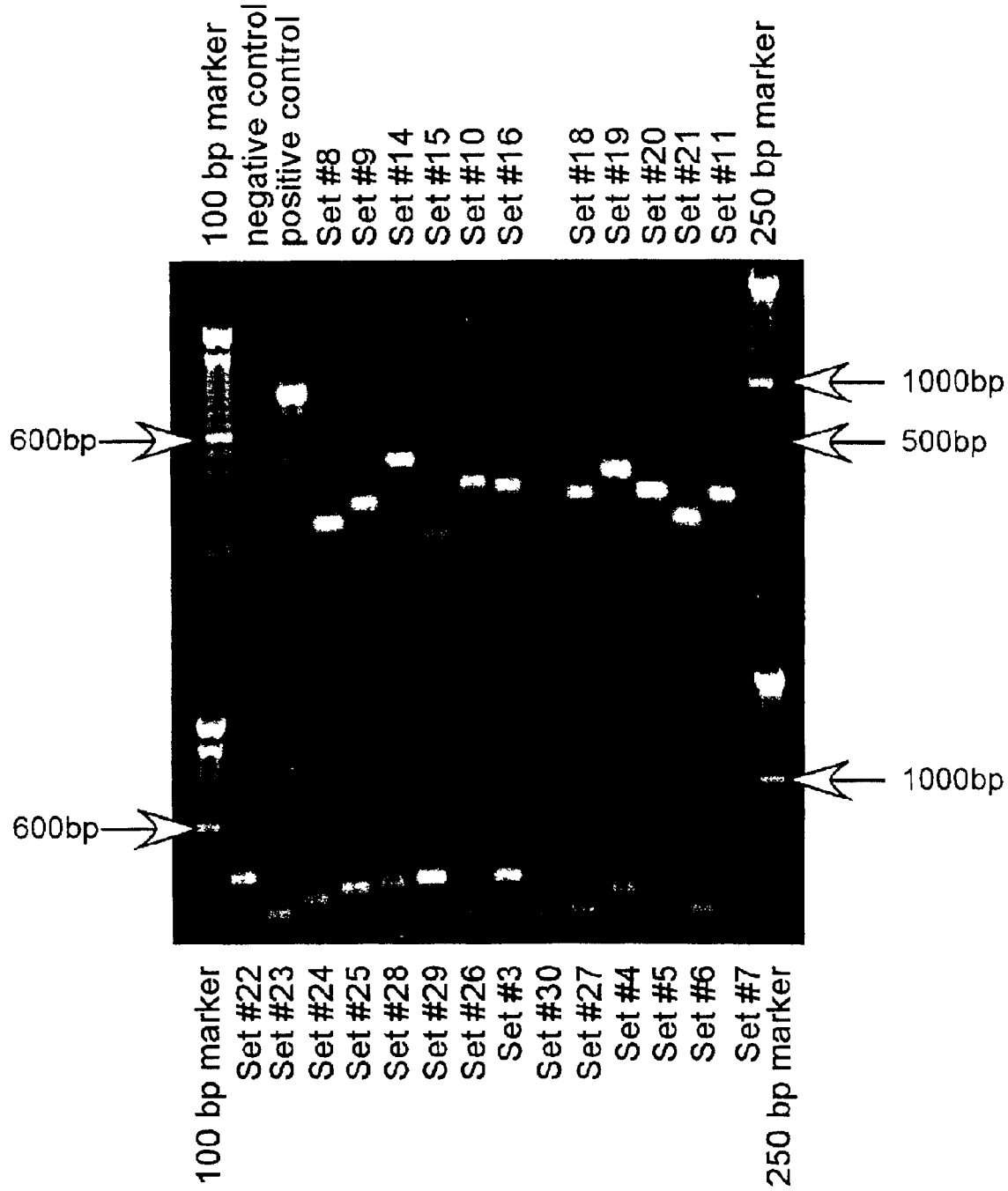
FIGS. 7A and 7B shows the detection by agarose gel electrophoresis and ethidium bromide staining of RT PCR-amplified group O isolate 3012 pol integrase fragments using all primer sets not shown in FIG. 5. Molecular weight bands corresponding to 600, 500 and 1000 bp markers are highlighted with arrows.
Figure 7B:
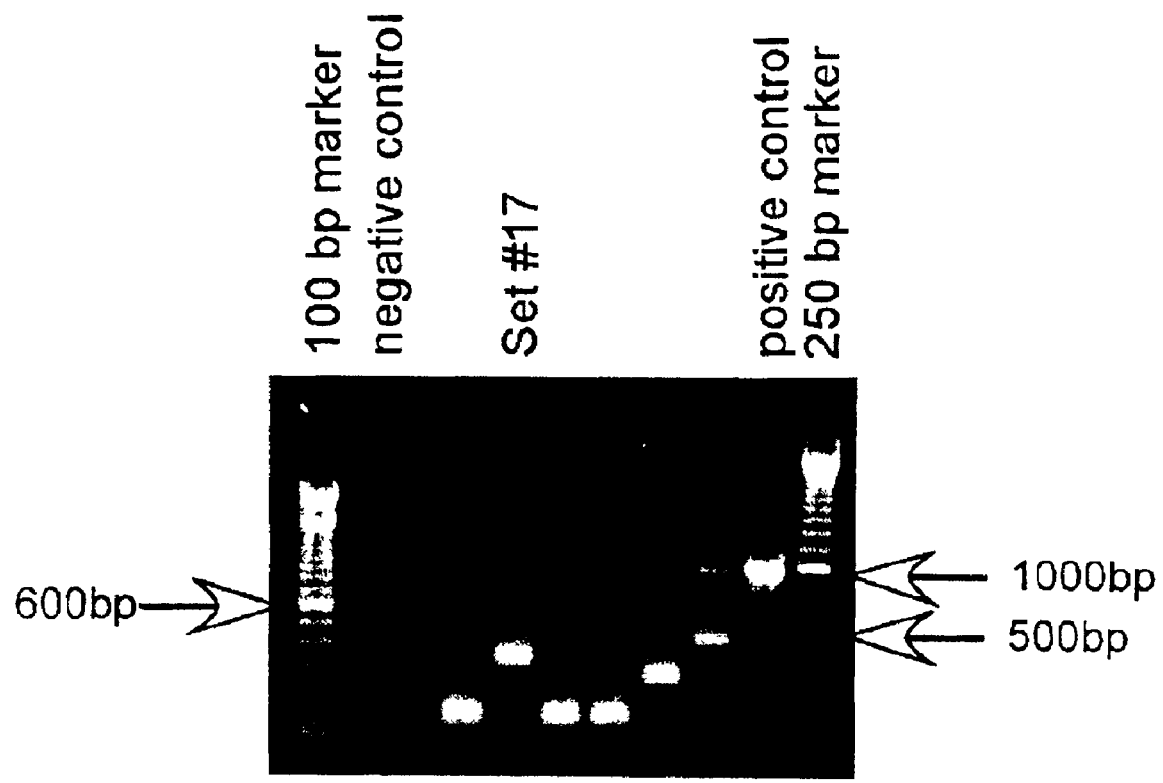

Reaction products were detected by agarose gel electrophoresis. From each 100 µl reaction, 5 µl was run on an agarose gel along with molecular weight markers to determine the length of the fragment. FIG. 4 shows a schematic of the expected fragment sizes and positions, relative to the integrase gene, for each primer set. Fragments were visualized after staining with ethidium bromide by exposure to UV light. A representative sampling of these data are shown (FIG. 5–FIG. 7). FIG. 5 shows amplification of each isolate with primer sets #1, #2, #12 and #13. FIGS. 6 and 7 show the amplification with all the remaining primer sets for two specific isolates: group M subtype CRF02_AG isolate DJ263 and group O isolate 3012. Data for all testing done in this experiment are summarized in Table 4 and show detection of HIV-1 group M subtypes A–G, as well as Group O, by HIV-1 primer sets #1–30.

For some fragments, the remaining portion of the reaction was then purified and sequenced to confirm amplification of the intended product. The purification was performed with either a QIAamp PCR purification kit or QIAquick gel extraction kit (Qiagen Inc.) according to the manufacturer's instructions. The purified PCR fragments were directly sequenced using the corresponding primers of the present invention, the ABI Prism Big Dye Terminator Cycle Sequencing Reaction Kit (PE Applied Biosystems, Foster City, Calif.) with AmpliTaq DNA polymerase FS, and an ABI model 377 automated sequencer (PE Applied Biosystems). Table 5 summarizes the sequencing results and demonstrates that the expected fragments were amplified.

TABLE 4

| HIV-1 Isolate | Subtype/ Group | Primer Sets (Designated in Table 1) | | | | | | | | | |
|---|---|---|---|---|---|---|---|---|---|---|---|
| | | 1 | 2 | 3 | 4 | 5 | 6 | 7 | 8 | 9 | 10 |
| BK132 | B | + | + | + | + | + | + | + | + | + | + |
| US1 | | + | + | + | + | + | + | + | + | + | + |
| SE364 | C | + | + | + | + | + | + | + | + | + | + |
| SM145 | | + | + | + | + | + | + | + | + | + | + |
| SE365 | D | + | + | + | + | + | + | + | + | + | + |
| UG274 | | + | + | + | + | + | + | + | + | + | + |
| CM238 | CRF01_AE | + | + | + | + | + | + | + | + | + | + |
| CM240 | | + | + | + | + | + | + | + | + | + | + |
| BZ126 | F | + | + | + | + | + | + | + | + | + | + |
| BZ163 | | + | + | + | + | + | + | + | + | + | + |
| MIKAG* | G | + | + | + | + | + | + | + | + | + | + |
| DJ263 | CRF02_AG | + | + | + | + | + | + | + | + | + | + |
| 08692A | Group O | + | + | + | + | + | + | + | + | + | + |
| 3012 | | + | + | + | + | + | + | + | + | + | + |

TABLE 4-continued

| HIV-1 Isolate | Subtype/ Group | Primer Sets (Designated in Table 1) | | | | | | | | | |
|---|---|---|---|---|---|---|---|---|---|---|---|
| | | 11 | 12 | 13 | 14 | 15 | 16 | 17 | 18 | 19 | 20 |
| BK132 | B | + | + | + | + | + | + | + | + | + | + |
| US1 | | + | + | + | + | + | + | + | + | + | + |
| SE364 | C | + | + | + | + | + | + | + | + | + | + |
| SM145 | | + | + | + | + | + | + | + | + | + | + |
| SE365 | D | + | + | + | + | + | + | + | + | + | + |
| UG274 | | + | + | + | + | + | + | + | + | + | + |
| CM238 | CRF01_AE | + | + | + | + | + | + | + | + | + | + |
| CM240 | | + | + | + | + | + | + | + | + | + | + |
| BZ126 | F | + | + | + | + | + | + | + | + | + | + |
| BZ163 | | + | + | + | + | + | + | + | + | + | + |
| MIKAG* | G | + | + | + | + | + | + | + | + | + | + |
| DJ263 | CRF02_AG | + | + | + | + | + | + | + | + | + | + |
| 08692A | Group O | + | + | + | + | + | + | + | + | + | + |
| 3012 | | + | + | + | + | + | + | + | + | + | + |

| HIV-1 Isolate | Subtype/ Group | Primer Sets (Designated in Table 1) | | | | | | | | | |
|---|---|---|---|---|---|---|---|---|---|---|---|
| | | 21 | 22 | 23 | 24 | 25 | 26 | 27 | 28 | 29 | 30 |
| BK132 | B | + | + | + | + | + | + | + | + | + | + |
| US1 | | + | + | + | + | + | + | + | nd | + | nd |
| SE364 | C | + | + | + | + | + | + | + | + | + | + |
| SM145 | | + | + | + | + | + | + | + | + | + | + |
| SE365 | D | + | + | + | + | + | + | + | + | + | + |
| UG274 | | + | + | + | + | + | + | + | + | + | + |
| CM238 | CRF01_AE | + | + | + | + | + | + | + | + | + | + |
| CM240 | | + | + | + | + | + | + | + | + | + | + |
| BZ126 | F | + | + | + | + | + | + | + | + | + | + |
| BZ163 | | + | + | + | + | + | + | + | + | + | + |
| MIKAG* | G | + | + | + | + | + | + | + | + | + | + |
| DJ263 | CRF02_AG | + | + | + | + | + | + | + | + | + | + |
| 08692A | Group O | + | + | + | + | + | + | + | + | + | + |
| 3012 | | + | + | + | + | + | + | + | + | + | + |

+ indicates that the expected fragment size was detected by agarose gel electrophoresis, ethidium bromide staining and visualization under UV light
"nd" indicates testing was not done
*MIKAG is the sample ID used internally for the isolate typically identified as HH8793 (Carr, J. K. et. al., Virology 247:22–31 (1998)).

TABLE 5

| HIV-1 Isolate | Subtype/Group in pol integrase | Primer Set Number | Expected fragment length | Fragment Sequence Verified* |
|---|---|---|---|---|
| CM238 | A | 4 | 229 | Yes |
| CM238 | A | 10 | 296 | Yes |
| CM240 | A | 19 | 353 | Yes |
| CM240 | A | 29 | 278 | Yes |
| US1 | B | 8 | 158 | Yes |
| BK132 | B | 26 | 128 | Yes |
| SE364 | C | 6 | 146 | Yes |
| SE364 | C | 14 | 416 | Yes |
| SM145 | C | 16 | 278 | Yes |
| UG274 | D | 5 | 155 | Yes |
| DJ263 | G | 17 | 353 | Yes |
| 3012 | Group O | 3 | 284 | Yes |
| 08692A | Group O | 9 | 224 | Yes |
| 3012 | Group O | 18 | 242 | Yes |

*Verification of correct amplified fragment determined by comparison to target isolate sequence.

HIV-1 primer sets #1–30 successfully detected all HIV-1 subtypes tested (Table 4), including the genetically divergent Group O isolates. For each primer set a fragment of the expected length was detected based on the agarose gel analysis. For those fragments which were sequenced, the sequence analysis confirms that each fragment amplified was the expected fragment based on comparison with the integrase sequence of the target isolate.

Example 4

HIV-1 Sensitivity

Two of the viral isolates described in Examples 2 and 3 were used to evaluate the sensitivity of the primer sets of Table 1. The isolates were diluted in defibrinated HIV-1-seronegative human plasma and were then tested using the Abbott LCx HIV Quantitative RNA Assay (Abbott Laboratories; Abbott Park, Ill.) to determine viral load. The diluted samples were then tested using primer sets 1–30 as described in Example 3. The two isolates chosen for testing were one group M isolate, UG274 (subtype D), at 1585 copies/ml and one group O isolate, 3012, at 1479 copies/ml.

The results of the sensitivity testing are summarized in Table 6. All primer sets successfully detected both isolates. One primer set (set #1) required slight modification of the PCR conditions to detect the group O isolate. Initial testing of the group O isolate with primer set #1 showed mixed results. The first test showed a very weak band of the expected fragment length on the agarose gel. However, repeat testing showed no band. Slight modification of the PCR conditions by lowering the annealing temperature during cycling from 50° C. to 45° C. improved the results and a clear band was detected by the agarose gel electrophoresis. The conditions described in Example 3 were designed for general screening of the primer sets against all of the isolates. The results for primer set #1 may indicate that, for optimal sensitivity, amplification conditions could be optimized specifically for each primer set.

These results show that the primer sets of this invention detect HIV-1 both group M and group O with sensitivity of at least 1500 copies/ml, the lowest concentration tested.

TABLE 6

| Primer Sets | HIV-1 Isolate, group | |
|---|---|---|
| (Designated in Table 1) | UG274, group M | 3012, group O |
| 1 | + | + |
| 2 | + | + |
| 3 | + | + |
| 4 | + | + |
| 5 | + | + |
| 6 | + | + |
| 7 | + | + |
| 8 | + | + |
| 9 | + | + |
| 10 | + | + |
| 11 | + | + |
| 12 | + | + |
| 13 | + | + |
| 14 | + | + |
| 15 | + | + |
| 16 | + | + |
| 17 | + | + |
| 18 | + | + |
| 19 | + | + |
| 20 | + | + |
| 21 | + | + |
| 22 | + | + |
| 23 | + | + |
| 24 | + | + |
| 25 | + | + |

TABLE 6-continued

| Primer Sets | HIV-1 Isolate, group | |
|---|---|---|
| (Designated in Table 1) | UG274, group M | 3012, group O |
| 26 | + | + |
| 27 | + | + |
| 28 | + | + |
| 29 | + | + |
| 30 | + | + |

Example 5

Detection of HIV-1 M and O Amplification Products Using Molecular Beacon Probes The primers employed to generate an amplification product that was detected using molecular beacon probes were SEQUENCE ID NO. 28, SEQUENCE ID NO. 29, SEQUENCE ID NO. 30, SEQUENCE ID NO. 31, SEQUENCE ID NO. 32, SEQUENCE ID NO. 33, SEQUENCE ID NO. 34, SEQUENCE ID NO. 35, SEQUENCE ID NO. 4, SEQUENCE ID NO. 37, SEQUENCE ID NO. 38, SEQUENCE ID NO. 22 and SEQUENCE ID NO. 40. Primer sequences were synthesized using standard oligonucleotide synthesis methodology. Primer sequences were used together in primer sets, as designated below in Table 7, for the detection of HIV (forward primers are shown as the top member of the pair, with the reverse primer being the bottom member of the pair).

TABLE 7

| Primer Set | Sequence (5'-3') | SEQ. ID. NO. |
|---|---|---|
| 31 | ATTCCCTACAATCCCCAAAGTCAAGGAGT | 28 |
|    | CCCCTGCACTGTACCCCCCAATCCC | 29 |
| 32 | ATTCCCTACAATCCCCAAAGTCAAGGAGT | 28 |
|    | CCTGCACTGTACCCCCCAATCC | 30 |
| 33 | ATTCCCTACAATCCCCAAAGTCAAGGAGT | 28 |
|    | CCAATCCCCCCTTTTCTTTTAAAATTGTC | 31 |
| 34 | ATTCCCTACAATCCCCAAAGTCAAGGAGT | 28 |
|    | TGTATTACTACTGCCCCTTCACCTTTCCA | 32 |
| 35 | ATTCCCTACAATCCCCAAAGTCAAGGAGT | 28 |
|    | ATCATCACCTGCCATCTGTTTTCCATA | 33 |
| 36 | CACAATTTTAAAAGAAAAGGGGGATTG | 34 |
|    | TGTATTACTACTGCCCCTTCACCTTTCC | 35 |
| 37 | CACAATTTTAAAAGAAAAGGGGGATTGG | 4 |
|    | ATCATCACCTGCCATCTGTTTTCCATA | 33 |
| 38 | TTTCGGGTTTATTACAGGGACAGCAGA | 37 |
|    | TGTATTACTACTGCCCCTTCACCTTTCCA | 32 |
| 39 | TTTCGGGTTTATTACAGGGACAGCAGA | 37 |
|    | ATCATCACCTGCCATCTGTTTTCCATA | 33 |

TABLE 7-continued

| Primer Set | Sequence (5'-3') | SEQ. ID. NO. |
|---|---|---|
| 40 | CTTAAGACAGCAGTACAAATGGCAGT | 38 |
|    | CCCCTGCACTGTACCCCCCAATCCC | 29 |
| 41 | CTTAAGACAGCAGTACAAATGGCAGT | 38 |
|    | CCTGCACTGTACCCCCCAATCC | 30 |
| 42 | CACAATTTTAAAAGAAAAGGGGGATTGG | 4 |
|    | TCTCTGCTGTCCCTGTAATA | 22 |
| 43 | CACAATTTTAAAAGAAAAGGGGGATTGG | 4 |
|    | TCTCTGCTGTCCCTGTAATAAACC | 40 |
| 44 | CACAATTTTAAAAGAAAAGGGGGATTG | 34 |
|    | TCTCTGCTGTCCCTGTAATA | 22 |
| 45 | CACAATTTTAAAAGAAAAGGGGGATTG | 34 |
|    | TCTCTGCTGTCCCTGTAATAAACC | 40 |

Example 6

Preparation of HIV Molecular Beacon Probes

Molecular beacon probes were designed to hybridize with the amplified HIV integrase target sequence by oligonucleotide hybridization. These probes were SEQUENCE ID NO. 41, SEQUENCE ID NO. 42, SEQUENCE ID NO. 43, SEQUENCE ID NO. 44, SEQUENCE ID NO. 45, SEQUENCE ID NO. 46, SEQUENCE ID NO. 47, SEQUENCE ID NO. 48, SEQUENCE ID NO. 49, SEQUENCE ID NO. 50, SEQUENCE ID NO. 51, SEQUENCE ID NO. 52, SEQUENCE ID NO. 53, SEQUENCE ID NO. 54, SEQUENCE ID NO. 55, SEQUENCE ID NO. 56, SEQUENCE ID NO. 57, SEQUENCE ID NO. 58, SEQUENCE ID NO. 59, SEQUENCE ID NO. 60, SEQUENCE ID NO. 61, SEQUENCE ID NO. 62, SEQUENCE ID NO. 63, SEQUENCE ID NO. 64 and SEQUENCE ID NO. 65. Probe sequences were synthesized using standard oligonucleotide synthesis methodology and labeled with the fluorophore 6-carboxyfluorescein (6-FAM) at the 5' end and C6-NH-DABCYL at the 3' end using standard cyanoethyl phosphoramidite coupling chemistry as described in U.S. Pat. No. 5,464,746 (herein incorporated by reference). The HIV molecular beacon probe sequences used are shown below in Table 8.

TABLE 8

| | Probe Sequence (5'–3') | SEQ. ID. NO. |
|---|---|---|
| A | gcgAG ACAGCAGTACAAATGGCA ctcgc | 41 |
| B | cgga ACAGCAGTACAAATGGCA tcca | 42 |
| C | atctCAC ACAGCAGTACAAATGGCA GTgagat | 43 |
| D | ctcCAC AGCAGTACAAATGGCA GTggag | 44 |
| E | ccACA GCAGTACAAATGGCAG Tgtgg | 45 |
| F | cggaAC AGCAGTACAAATGGCA GTtccg | 46 |
| G | accgtA CAGCAGTACAAATGGCAGTAT Tacggt | 47 |
| H | ccgttt ACAGCAGTACAAATGGCAGTATTCA aaacgg | 48 |
| I | CACAGCA CACAGCAGTACAAATGGCAGTATTCATCCACAATTTTAA tgctgtg | 49 |
| J | cttactC ACAATTTTAAAAGAAAA Gagtaag | 50 |
| K | cttactC ACAATTTTAAAAGAAAAG Gagtaag | 51 |
| L | ctgactC ACAATTTTAAAAGAAAAGG Gagtcag | 52 |
| M | gtacC ACAATTTTAAAAGAAAAG GGtac | 53 |
| O | acgcc tAATTTTCGGGTTTATTACAG GGcgt | 54 |
| P | catcCT TTGGAAAGGACCAGC Aggatg | 55 |
| Q | caccCT CTGGAAAGGTGAAGGGGCAGT AGggtg | 56 |
| R | tcgacA AAGGTGAAGGGGCAGTAG Tgtcga | 57 |

In Table 8 above, capital letters represent sequences specific to HIV, lower case letters represent random sequences used to generate the stem of the molecular beacon probe, and the boxed regions are the sequences that form the stem.

Probes A (SEQ. ID. NO. 41), B (SEQ. ID. NO. 42), C (SEQ. ID. NO. 43), D (SEQ. ID. NO. 44), E (SEQ. ID. NO. 45), F (SEQ. ID. NO. 46), G (SEQ. ID. NO. 47) and H (SEQ. ID. NO. 48) can be used with primer sets 31, 32, 33, 34 and 35; probe I (SEQ. ID. NO. 49) can be used with primer sets 31, 32, 34 and 35; probes J (SEQ. ID. NO. 50), K (SEQ. ID. NO. 51), L (SEQ. ID. NO. 52), and M (SEQ. ID. NO. 53) can be used with primer sets 31, 32, 34, 35, 40 and 41; probe O (SEQ. ID. NO. 54) can be used with primer sets 34, 35, 36 and 37; probe P (SEQ. ID. NO. 55) can be used with primer sets 34, 35, 36, 37, 38 and 39; and probes Q (SEQ. ID. NO. 56) and R (SEQ. ID. NO. 57) can be used with primers sets 35, 37 and 39.

Example 7

Sensitivity of Primer Sets with Molecular Beacon Probes

Performance of the primer sets, prepared as in Example 5 and shown in Table 7, was assessed using dilutions of an HIV RNA sample (Abravaya, K, et al, J Clin Microbiol, 38: 716–723 (2000)) with selected molecular beacon probes, prepared as in Example 6 and shown in Table 8. Purified HIV RNA was diluted to 100,000 copies/ml, 10,000 copies/ml, 1000 copies/ml, 100 copies/ml and 25 copies/ml, then reverse transcribed, PCR amplified and detected in separate reactions utilizing various primer set/probe combinations. A negative control containing no HIV RNA was also included with each primer set/probe combination. RT-PCR was performed in a 100 μl reaction mixture containing 130 nM of the appropriate forward primer, 478 nM of the appropriate reverse primer, 81 nM of the appropriate HIV molecular beacon probe, 4.38 mM $MnCl_2$, 0.375 mM of each dNTP (dATP, dGTP, dTTP and dCTP), 13 units of recombinant *Thermus thermophilus* polymerase, Bicine buffer and HIV RNA dilution or negative control.

Reaction mixtures were reverse transcribed and amplified in a Perkin-Elmer 9700 Thermal Cycler. Reaction mixtures were first incubated at 59° C. for 30 minutes to reverse transcribe the RNA, followed by 4 cycles of 95° C. for 30 seconds, 54° C. for 30 seconds and 72° C. for 30 seconds. Further amplification was then accomplished with 36 to 40 cycles at 90° C. for 30 seconds, 59° C. for 30 seconds and 72° C. for 30 seconds. After the reaction mixtures were thermal cycled, probe oligo hybridization was accomplished by raising the mixtures to 94° C. for 5 seconds then lowering the temperature to 45° C. for 15 seconds, followed by 25° C. for 10 seconds. Samples were held at 25° C. until detection of reaction products. Reaction products were detected using a fluorescent reader, such as the Cytofluor (Perceptive; Framingham, Mass.) or BioTek 600 (Applied Biosystems, Foster City, Calif.). Results are expressed in fluorescent units and are shown in Table 9 below.

TABLE 9

| Primer Set/ Probe | HIV RNA Concentration (copies/ml) | | | | | |
|---|---|---|---|---|---|---|
| | 0 | 25 | 100 | 1000 | 10,000 | 100,000 |
| 31/A | 2103 * | 9351 | 11,477 * | 34,600 * | 61,587 * | 80,751 |
| 32/A | 1167 * | 3396 | 5915 * | 21,031 * | 46,082 * | 50,989 |
| 33/A | 1914 | 2716 | 2904 | 3427 | 6588 | 21,149 |
| 34/A | 1948 | 2851 | 3025 | 2784 | 3352 | 5931 |
| 35/A | 1418 | 2045 | 2007 | 2223 | 2121 | 2709 |
| 36/P | 3347 | 4884 | 6162 | 5660 | 6253 | 9190 |
| 37/P | 6309 | 6592 | 7470 | 7815 | 8378 | 8491 |
| 38/P | 1599 | 11,721 | 19,634 | 40,023 | 62,986 | NT |
| 39/P | 4314 | 5244 | 7447 | 8939 | 15,112 | 30,633 |
| 40/M | 4078 | 2177 | 2272 | 3668 | 6131 | 20,734 |
| 41/M | 3940 | 4292 | 3548 | 6765 | 29,004 | 58,700 |

* Results are the average from two experiments.
NT: Not Tested.

Primer sets 31, 32, and 38 gave the best performance, detecting 25 copies/ml of HIV, easily distinguished from the negative control (0 copies/ml). Primer sets 33, 39, 40 and 41 detected 1000 to 10,000 copies/ml of HIV. Though primer sets 34, 35, 36 and 37 did not perform as well, this was not due to the probe used since probe A or P did show good results when used with other primer sets.

Primer sets 42, 43, 44 and 45 were also tested as above, but without the probe annealing step. Results were analyzed by running gels with the RT-PCR products. The expected band was visible using 10,000 copies/ml of HIV.

Example 8

Sensitivity of Molecular Beacon Probes

Performance of the molecular beacon probes A through M, prepared as in Example 6 and shown in Table 8, was assessed by testing dilutions of HIV RNA as in Example 7 above, with primer set 32, prepared as in Example 5. Similarly, probe O was used with primer set 35, and probes P, Q and R were used with primer set 39. Results are shown below in Table 10.

TABLE 10

| Probe/ Primer Set | HIV RNA Concentration (copies/ml) | | | | | |
|---|---|---|---|---|---|---|
| | 0 | 25 | 100 | 1000 | 10,000 | 100,000 |
| A/32 | 3,677 | 8,576 | 12,146 | 34,960 | NT | 56,174 |
| B/32 | 1,903 | 3,410 | 5,104 | 11,774 | 25,845 | 41,580 |
| C/32 | 50,358 | 54,011 | 55,097 | 60,032 | 65,914 | 74,810 |
| D/32 | 22,822 | 24,670 | 25,162 | 29,706 | 38,057 | 52,024 |
| E/32 | 3,873 | 11,193 | 15,319 | 42,271 | NT | 59,370 |
| F/32 | 6,041 | 6,447 | 6,372 | 7,348 | 8,272 | 10,759 |
| G/32 | 14,213 | 15,582 | 16,874 | 25,797 | 43,201 | 63,271 |
| H/32 | 5,795 | 11,068 | 15,553 | 41,118 | NT | 51,347 |
| I/32 | 6,300 | 12,259 | 16,921 | 40,591 | NT | 51,280 |
| J/32 | 8,816 | 10,858 | 11,357 | 17,149 | 25,053 | 31,438 |
| K/32 | 9,099 | 11,223 | 12,826 | 26,377 | 46,112 | 59,508 |
| L/32 | 40,578 | 44,234 | 45,760 | 46,854 | 48,856 | 53,210 |
| M/32 | 2,079 | 3,307 | 4,176 | 11,356 | 26,509 | 40,455 |
| O/35 | 3,502 | 4,561 | 5,728 | 5,433 | 5,322 | 6,840 |
| P/39 | 4,314 | 5,244 | 7,447 | 8,939 | 15,112 | 30,633 |
| Q/39 | −178 | −1,678 | −2,353 | −114 | 9,933 | 41,434 |
| R/39 | 8,295 | 8,975 | 10,129 | 10,811 | 26,606 | 53,356 |

NT: Not Tested.

Probes A, B, E, H and I detected 25 copies/ml of HIV and distinguished this amount from the negative control (0 copies/ml). Probes J, K, M, P and R detected 100 to 1000 copies/ml of HIV. Probes F, O and Q were less efficient, and probes C, D, G and L gave higher background values with the negative control. The performance differences observed with probes C, D, E and F were surprising since they had the same HIV binding sequence. However, they only differ in the composition of the stem sequences. Probes J, K and L were also surprising, in that they only differed by one base in their HIV binding sequence and had identical or very similar stem sequence compositions. Probes J and K detected HIV at approximately 1000 copies/ml whereas probe L gave higher background values than J or K.

Example 9

Sensitivity of Molecular Beacon Probes with Indole or Inosine Substitutions

Probes A, B, E, H and I, were analyzed against 325 known HIV-1 sequences. Sites with the most common mismatches were identified and the probes were modified to contain a universal base at the mismatched positions. The mismatched positions within the probes were substituted with nitro-indole or inosine as shown in Table 11. These modified probes were synthesized as in Example 6. The sequences of these modified probes are shown below in Table 11.

TABLE 11

| Probe | Sequence (5'–3') | SEQ. ID. NO. |
|---|---|---|
| A1 | gcgAGACAGCAGTACANATGGCActcgc | 58 |
| B1 | cggaACAGCAGTACANATGGCAtccg | 59 |
| E1 | ccACAGCAGTACANATGGCAGTgtgg | 60 |
| H1 | ccgtttACAGCAGTACANATGGCAGTATTCAaaacgg | 61 |
| Eino | ccACAGCAGTACAIATGGCAGTgtgg | 62 |
| Hino | ccgtttACAGCAGTACAIATGGCAGTATTCAaaacgg | 63 |
| Iino | CACAGCAGTACAAATGGCAGTATTCATICACAATTTTAAtgctgtg | 64 |
| Iino2 | CACAGCAGTACAIATGGCAGTATTCATICACAATTTTAAtgctgtg | 65 |

N: Indole
I: Inosine

Performance of the indole or inosine molecular beacon probes was assessed by testing dilutions of HIV RNA as in Example 7 above, with primer set 32, prepared as in Example 5. Results are shown below in Table 12. All probes that contained indole or inosine substitutions detected 25 copies/ml of HIV and distinguished this amount from the negative control (0 copies/ml).

TABLE 12

| | HIV RNA Concentration (copies/ml) | | | | | |
|---|---|---|---|---|---|---|
| Probe | 0 | 25 | 100 | 1000 | 10,000 | 100,000 |
| A1 | 669 | 1,381 | 2,650 | 7,561 | 19,305 | 32,949 |
| B1 | 4,774 | 6,415 | 8,035 | 13,758 | 23,041 | 33,279 |
| E1 | 3,943 | 7,162 | 8,696 | 20,493 | 38,823 | 56,091 |
| H1 | 1,903 | 3,281 | 5,507 | 12,706 | 30,425 | 48,131 |
| Eino | 4,894 | 11,911 | 13,906 | 34,961 | 50,555 | 62,953 |
| Hino | 6,444 | 10,869 | 16,542 | 40,353 | 49,053 | 54,063 |
| Iino | 8,217 | 16,767 | 20,793 | 49,331 | 65,591 | 75,008 |
| Iino2 | 8,169 | 14,273 | 20,896 | 52,639 | 72,729 | 78,684 |

Example 10

Detection of Different HIV Subtypes with Molecular Beacon Probes

Different HIV subtypes were obtained and RNA was isolated as described in Abravaya, K, et al, J Clin Microbiol, 38: 716–723 (2000) and in Johanson J, et al, J Virol Methods, 95: 81–92 (2001). Isolated HIV RNA from these different subtypes was diluted to approximately 1000 copies/ml and tested as described in Example 7 by RT-PCR and probe oligo hybridization using primer set 32 with probe A, primer set 32 with probe H or primer set 38 with probe P. Primer sets used were as described in Example 5 and probes used were as described in Example 6. Reaction products were detected using a fluorescent reader (as described in Example 7) and expressed in fluorescent units. As can be seen in Table 13 below, all HIV subtypes were detected with the three primer/probe sets tested.

TABLE 13

| Subtype/ Group | Sample ID | Primer Set 32 & Probe A | Primer Set 32 & Probe H | Primer Set 38 & Probe P |
|---|---|---|---|---|
| A | 422 | 20,501 | 41,503 | 32,465 |
| | 327 | 7,308 | 20,296 | 36,468 |
| | 312 | 24,360 | 49,007 | 26,481 |
| | 419 | 29,44 | 51,112 | 34,378 |
| B | t1600 | 27,660 | 49,467 | 20,334 |
| | t1273 | 25,396 | 48,658 | 41,079 |
| | t50788 | 19,239 | 38,155 | 27,698 |
| D | 306 | NT | 20,437 | 15,807 |
| | 308 | 6,171 | 34,772 | 22,959 |
| | 418 | 14,863 | 44930 | 29,918 |
| CRF01_AE | 155 | 14,460 | 51,900 | 47,237 |
| | 577 | 11,429 | 52,058 | 44,851 |
| | 1102 | 14,933 | 48,197 | 48,147 |
| | 50436 | 16,213 | 47,370 | 46,162 |
| F | Br97 | 24,661 | 43,367 | 32,467 |
| | Br112 | 23,503 | 43,043 | 25,331 |
| | Br58 | 26,642 | 42,463 | 27,637 |
| | Br41 | 17,728 | 47,758 | 35,496 |
| | Br57 | 11,335 | 56,803 | 30,719 |
| G* | 3671 | 30,315 | 56,658 | 47,201 |
| O | 11897755A (08692A) | 29,736 | 57,056 | 46,569 |
| Negative Control | | 951 | 2,189 | 1,068 |
| Positive Control | Subtype B RNA transcript | 18,253 | 35,279 | 40,421 |

NT: Not Tested.
*This isolate is an intersubtype recombinant between subtypes A and G. The pol integrase region is subtype G.

RNA transcripts were generated from clones of HIV subtypes A, C, D, CRF01_AE and F, as described in Abravaya, K, et al, J Clin Microbiol, 38: 716–723 (2000) and in Johanson J, et al, J Virol Methods, 95: 81–92 (2001). Transcripts were diluted to approximately 10,000 copies/ml, amplified and detected as described in example 8 using primer set 32 with either probe A or probe H. The results in Table 14 show that all HIV subtypes tested were detected with the two primer/probe sets used.

TABLE 14

| Subtype | Primer Set 32 & Probe A | Primer Set 32 & Probe H |
|---|---|---|
| A | 12,626 | 62,852 |
| C | 44,322 | 65,210 |
| D | 51,682 | 79,109 |
| CRF01_AE | 42,098 | 74,776 |
| F | 35,517 | 73,741 |
| Negative Control | 1,386 | 3,213 |
| Positive Control (B) | 52,259 | 53,336 |

Example 11

Quantitation of Different HIV Subtypes with Molecular Beacon Probes

The RNA isolated from the different HIV subtypes described in Example 10, was diluted to approximately 1000 (or 3 log) copies/ml and tested as described in Example 7 using primer set 32 with probe A or primer set 32 with probe H. In order to achieve quantitative results, the RT-PCR reaction mixture also contained 0.1 µM of a molecular beacon probe (SEQ ID NO. 66: gcgaGACGAGTTCATGAGGGCAGctcgc) specific for an Internal Control transcript sequence, and 500 copies/reaction of the Internal Control transcript (SEQ ID NO. 67). The IC transcript has the same primer binding sites as HIV and a specific IC probe binding region. The IC probe is synthesized as in Example 6 but labeled with a different fluorophore, sulforhodamine 101 (Texas Red), at the 5' end post-synthetically using a C6-NH-derivated probe at the 5' end conjugated with sulphonyl chloride-derivatized sulforhodamine 101. In this competitive format, the signal from the HIV probe increases while the signal from the IC probe decreases as the concentration of target HIV increases. A calibration curve was generated by dividing the log of the HIV probe signal by the log of the IC probe signal, and HIV samples were then quantitated using this calibration curve.

The results of quantifying the RNA isolates from the different HIV subtypes by this method are shown in Table 15, with values expressed as log copies/ml. With the exception of the subtype A isolate 327, all isolates tested were quantitated at approximately 3 log copies/ml. This isolate also was tested with primer set 31, which is identical to primer set 32 except that the reverse primer is 3 bases longer (see Table 7; two additional nucleotides at the 5' end and one additional nucleotide at the 3' end), the signal was twice as high (data not shown).

TABLE 15

| Subtype/Group | Sample ID | Primer Set 32 & Probe A | Primer Set 32 & Probe H |
|---|---|---|---|
| A | 422 | 3.59 | 3.66 |
|  | 327 | 1.72 | 1.98 |
|  | 312 | 3.50 | 3.55 |
|  | 419 | 3.38 | 3.43 |
| B | t1600 | 3.48 | 3.46 |
|  | t1273 | 3.11 | 3.15 |
|  | t50788 | 3.18 | 3.26 |
| D | 306 | 2.96 | 2.87 |
|  | 308 | 3.31 | 3.26 |
|  | 418 | 3.41 | 3.38 |
| CRF01_AE | 155 | 3.18 | 3.23 |
|  | 577 | 3.47 | 3.52 |
|  | 1102 | 3.44 | 3.48 |
|  | 50436 | 3.38 | 3.44 |
| F | Br97 | 3.48 | 3.48 |
|  | Br112 | 3.41 | 3.42 |
|  | Br58 | 3.33 | 3.40 |
|  | Br41 | 3.46 | 3.44 |
|  | Br57 | 3.65 | 3.61 |
| G* | 3671 | 3.52 | 3.59 |
| O | 11897755 A (08692A) | 3.69 | 3.81 |

*This isolate is an intersubtype recombinant between subtypes A and G. The pol integrase region is subtype G.

Similarly, the RNA transcripts generated from clones of the HIV-1 isolates representing subtypes A, C, D, CRF01_AE and F, as described in Example 10, were diluted to approximately 10,000 copies/ml, and quantitated as described above in example 11 using primer set 32 with either probe A or probe H. Results in Table 16 show that almost all HIV transcripts (see Abravaya, K, et al, J Clin Microbiol, 38: 716–723 (2000)) were quantitated at 4 log copies/ml.

TABLE 16

| Subtype | Primer Set 32 & Probe A | Primer Set 32 & Probe H |
|---|---|---|
| A | 3.02 | 3.99 |
| C | 4.10 | 3.92 |
| D | 4.31 | 4.15 |
| CRF01_AE | 4.12 | 4.04 |
| F | 4.06 | 4.02 |

While the invention has been described in detail and with reference to specific embodiments, it will be apparent to one skilled in the art that various changes and modifications may be made to such embodiments without departing from the spirit and scope of the invention.

What is claimed is:

1. A probe selected from the group consisting of:
SEQ ID NO: 41; SEQ ID NO: 42; SEQ ID NO: 43; SEQ ID NO: 44; SEQ ID NO: 45; SEQ ID NO: 46; SEQ ID NO: 47; SEQ ID NO: 48; SEQ ID NO: 49; SEQ ID NO: 58; SEQ ID NO: 59; SEQ ID NO: 60; SEQ ID NO: 61; SEQ ID NO: 62; SEQ ID NO: 63; SEQ ID NO: 64; and SEQ ID NO: 65.

2. The probe of claim 1, wherein the probe is selected from the group consisting of: SEQ ID NO: 41; SEQ ID NO: 42; SEQ ID NO: 45; SEQ ID NO: 48; and SEQ ID NO: 49.

3. A method for detecting the presence of HIV-1 in a test sample comprising:
   contacting a test sample with amplification reagents;
   placing the reaction mixture under amplification conditions to form an amplification product;
   forming a hybrid between the amplification product and a probe selected from the group consisting of SEQ ID NO: 41; SEQ ID NO: 42; SEQ ID NO: 43; SEQ ID NO: 44; SEQ ID NO: 45; SEQ ID NO: 46; SEQ ID NO: 47; SEQ ID NO: 48; SEQ ID NO: 49; SEQ ID NO: 58; SEQ ID NO: 59; SEQ ID NO: 60; SEQ ID NO: 61; SEQ ID NO: 62; SEQ ID NO: 63; SEQ ID NO: 64; and SEQ ID NO: 65; and
   detecting the hybrid as an indication of the presence of HIV-1 in the test sample.

4. The method of claim 3 wherein the hybrid is formed while the reaction mixture is under amplification conditions.

5. The method of claim 3,
   wherein the probe is selected from the group consisting of SEQ ID NO: 41, SEQ ID NO: 42, SEQ ID NO: 43, SEQ ID NO: 44, SEQ ID NO: 45, SEQ ID NO: 46, SEQ ID NO: 47 and SEQ ID NO: 48, and
   wherein the amplification reagents comprise SEQ ID NO: 28.

6. The method of claim 5, wherein the amplification reagents include a primers selected from the group consisting of:
   SEQ ID NO: 28 and SEQ ID NO: 29, SEQ ID NO: 28 and SEQ ID NO: 30, SEQ ID NO: 28 and SEQ ID NO: 31, SEQ ID NO: 28 and SEQ ID NO: 32, and SEQ ID NO: 28 and SEQ ID NO: 33.

7. The method of claim 3, wherein the probe comprises SEQ ID NO: 49 and wherein the amplification reagents comprise SEQ ID NO: 28.

8. The method of claim 7, wherein the amplification reagents include a primers selected from the group consisting of:
   SEQ ID NO: 28 and SEQ ID NO: 29, SEQ ID NO: 28 and SEQ ID NO: 30, SEQ ID NO: 28 and SEQ ID NO: 32, and SEQ ID NO: 28 and SEQ ID NO: 33.

* * * * *

SEQUENCE LISTING

<160> NUMBER OF SEQ ID NOS: 67

<210> SEQ ID NO 1
<211> LENGTH: 23
<212> TYPE: DNA

```
<213> ORGANISM: Artificial Sequence
<220> FEATURE:
<223> OTHER INFORMATION: Primer

<400> SEQUENCE: 1
ccaggaatat ggcaattaga ttg                                          23

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
cctgccatct gttttccata                                              20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gcagtccatg tagccagtgg                                              20

<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4
cacaatttta aagaaaagg ggggattgg                                     29

<210> SEQ ID NO 5
<211> LENGTH: 28
<212> TYPE: DNA
<213> ORGANISM: Artificial Sequence
<220> FEATURE:
<223> OTHER INFORMATION: Primer

<400> SEQUENCE: 5
tagacataat agcaacagac atacaaac                                     28

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tattacaggg acagcagaga                                              20

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7
gacagcagag acccaatttg gaaaggacc                                    29
```

```
<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
tggaaaggtg aagggcagt agt                                              23

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
aattggagag caatggctag tga                                             23

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ccttctaaat gtgtacaatc                                                 20

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
tctgctggga taacttctgc ttcta                                           25

<210> SEQ ID NO 12
<211> LENGTH: 32
<212> TYPE: DNA
<213> ORGANISM: Artificial Sequence
<220> FEATURE:
<223> OTHER INFORMATION: Primer

<400> SEQUENCE: 12
ttattcatag attctactac tccttgactt tg                                   32

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
aaggcagcct gttggtgg                                                   18

<210> SEQ ID NO 14
<211> LENGTH: 28
<212> TYPE: DNA
<213> ORGANISM: Artificial Sequence
<220> FEATURE:
```

```
<223> OTHER INFORMATION: Primer

<400> SEQUENCE: 14
gtttgtatgt ctgttgctat tatgtcta                              28

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
actactgccc cttcaccttt cca                                   23

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
gattgtacac atttagaagg                                       20

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
aatactgcca tttgtactgc tgt                                   23

<210> SEQ ID NO 18
<211> LENGTH: 32
<212> TYPE: DNA
<213> ORGANISM: Artificial Sequence
<220> FEATURE:
<223> OTHER INFORMATION: Primer

<400> SEQUENCE: 18
cccccaatcc cccttttct tttaaaattg tg                          32

<210> SEQ ID NO 19
<211> LENGTH: 33
<212> TYPE: DNA
<213> ORGANISM: Artificial Sequence
<220> FEATURE:
<223> OTHER INFORMATION: Primer

<400> SEQUENCE: 19
aagatggcca gtaaagtaa tacacacaga caa                         33

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
acccgaaaat tttgaattttt t                                    21
```

<210> SEQ ID NO 21
<211> LENGTH: 32
<212> TYPE: DNA
<213> ORGANISM: Artificial Sequence
<220> FEATURE:
<223> OTHER INFORMATION: Primer

<400> SEQUENCE: 21
caaagtcaag gagtagtaga atctatgaat aa                          32

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
tctctgctgt ccctgtaata                                        20

<210> SEQ ID NO 23
<211> LENGTH: 29
<212> TYPE: DNA
<213> ORGANISM: Artificial Sequence
<220> FEATURE:
<223> OTHER INFORMATION: Primer

<400> SEQUENCE: 23
ggtcctttcc aaattgggtc tctgctgtc                              29

<210> SEQ ID NO 24
<211> LENGTH: 23
<212> TYPE: DNA
<213> ORGANISM: Artificial Sequence
<220> FEATURE:
<223> OTHER INFORMATION: Primer polI8

<400> SEQUENCE: 24
tagtgggatg tgtacttctg aac                                    23

<210> SEQ ID NO 25
<211> LENGTH: 24
<212> TYPE: DNA
<213> ORGANISM: Artificial Sequence
<220> FEATURE:
<223> OTHER INFORMATION: Primer polI5

<400> SEQUENCE: 25
cacacaaagg rattggagga aatg                                   24

<210> SEQ ID NO 26
<211> LENGTH: 22
<212> TYPE: DNA
<213> ORGANISM: Artificial Sequence
<220> FEATURE:
<223> OTHER INFORMATION: Primer O-polI8

<400> SEQUENCE: 26
gattyctgga ttcataatga tg                                     22

<210> SEQ ID NO 27
<211> LENGTH: 21
<212> TYPE: DNA
<213> ORGANISM: Artificial Sequence
<220> FEATURE:
<223> OTHER INFORMATION: Primer O-polI5

```
<400> SEQUENCE: 27
gtatcttaca tgggttcctg c                                              21

<210> SEQ ID NO 28
<211> LENGTH: 29
<212> TYPE: DNA
<213> ORGANISM: Artificial Sequence
<220> FEATURE:
<223> OTHER INFORMATION: Primer

<400> SEQUENCE: 28
attccctaca atccccaaag tcaaggagt                                      29

<210> SEQ ID NO 29
<211> LENGTH: 25
<212> TYPE: DNA
<213> ORGANISM: Artificial Sequence
<220> FEATURE:
<223> OTHER INFORMATION: Primer

<400> SEQUENCE: 29
cccctgcact gtaccccca atccc                                           25

<210> SEQ ID NO 30
<211> LENGTH: 22
<212> TYPE: DNA
<213> ORGANISM: Artificial Sequence
<220> FEATURE:
<223> OTHER INFORMATION: Primer

<400> SEQUENCE: 30
cctgcactgt accccccaat cc                                             22

<210> SEQ ID NO 31
<211> LENGTH: 29
<212> TYPE: DNA
<213> ORGANISM: Artificial Sequence
<220> FEATURE:
<223> OTHER INFORMATION: Primer

<400> SEQUENCE: 31
ccaatccccc cttttctttt aaaattgtc                                      29

<210> SEQ ID NO 32
<211> LENGTH: 29
<212> TYPE: DNA
<213> ORGANISM: Artificial Sequence
<220> FEATURE:
<223> OTHER INFORMATION: Primer

<400> SEQUENCE: 32
tgtattacta ctgccccttc acctttcca                                      29

<210> SEQ ID NO 33
<211> LENGTH: 27
<212> TYPE: DNA
<213> ORGANISM: Artificial Sequence
<220> FEATURE:
<223> OTHER INFORMATION: Primer

<400> SEQUENCE: 33
atcatcacct gccatctgtt ttccata                                        27

<210> SEQ ID NO 34
<211> LENGTH: 28
```

```
<212> TYPE: DNA
<213> ORGANISM: Artificial Sequence
<220> FEATURE:
<223> OTHER INFORMATION: Primer

<400> SEQUENCE: 34
cacaatttta aagaaaagg ggggattg                                    28

<210> SEQ ID NO 35
<211> LENGTH: 28
<212> TYPE: DNA
<213> ORGANISM: Artificial Sequence
<220> FEATURE:
<223> OTHER INFORMATION: Primer

<400> SEQUENCE: 35
tgtattacta ctgccccttc acctttcc                                   28

<210> SEQ ID NO 36
<211> LENGTH: 29
<212> TYPE: DNA
<213> ORGANISM: Artificial Sequence
<220> FEATURE:
<223> OTHER INFORMATION: Primer

<400> SEQUENCE: 36
cacaatttta aagaaaagg ggggattgg                                   29

<210> SEQ ID NO 37
<211> LENGTH: 27
<212> TYPE: DNA
<213> ORGANISM: Artificial Sequence
<220> FEATURE:
<223> OTHER INFORMATION: Primer

<400> SEQUENCE: 37
tttcgggttt attacaggga cagcaga                                    27

<210> SEQ ID NO 38
<211> LENGTH: 26
<212> TYPE: DNA
<213> ORGANISM: Artificial Sequence
<220> FEATURE:
<223> OTHER INFORMATION: Primer

<400> SEQUENCE: 38
cttaagacag cagtacaaat ggcagt                                     26

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
tctctgctgt ccctgtaata                                            20

<210> SEQ ID NO 40
<211> LENGTH: 24
<212> TYPE: DNA
<213> ORGANISM: Artificial Sequence
<220> FEATURE:
<223> OTHER INFORMATION: Primer

<400> SEQUENCE: 40
```
tctctgctgt ccctgtaata aacc                                          24

<210> SEQ ID NO 41
<211> LENGTH: 28
<212> TYPE: DNA
<213> ORGANISM: Artificial Sequence
<220> FEATURE:
<223> OTHER INFORMATION: Probe A

<400> SEQUENCE: 41
gcgagacagc agtacaaatg gcactcgc                                      28

<210> SEQ ID NO 42
<211> LENGTH: 26
<212> TYPE: DNA
<213> ORGANISM: Artificial Sequence
<220> FEATURE:
<223> OTHER INFORMATION: Probe B

<400> SEQUENCE: 42
cggaacagca gtacaaatgg catccg                                        26

<210> SEQ ID NO 43
<211> LENGTH: 30
<212> TYPE: DNA
<213> ORGANISM: Artificial Sequence
<220> FEATURE:
<223> OTHER INFORMATION: Probe C

<400> SEQUENCE: 43
atctcacagc agtacaaatg gcagtgagat                                    30

<210> SEQ ID NO 44
<211> LENGTH: 28
<212> TYPE: DNA
<213> ORGANISM: Artificial Sequence
<220> FEATURE:
<223> OTHER INFORMATION: Probe D

<400> SEQUENCE: 44
ctccacagca gtacaaatgg cagtggag                                      28

<210> SEQ ID NO 45
<211> LENGTH: 26
<212> TYPE: DNA
<213> ORGANISM: Artificial Sequence
<220> FEATURE:
<223> OTHER INFORMATION: Probe E

<400> SEQUENCE: 45
ccacagcagt acaaatggca gtgtgg                                        26

<210> SEQ ID NO 46
<211> LENGTH: 28
<212> TYPE: DNA
<213> ORGANISM: Artificial Sequence
<220> FEATURE:
<223> OTHER INFORMATION: Probe F

<400> SEQUENCE: 46
cggaacagca gtacaaatgg cagttccg                                      28

<210> SEQ ID NO 47
<211> LENGTH: 33
<212> TYPE: DNA
<213> ORGANISM: Artificial Sequence

```
<220> FEATURE:
<223> OTHER INFORMATION: Probe G

<400> SEQUENCE: 47
accgtacagc agtacaaatg gcagtattac ggt                                  33

<210> SEQ ID NO 48
<211> LENGTH: 37
<212> TYPE: DNA
<213> ORGANISM: Artificial Sequence
<220> FEATURE:
<223> OTHER INFORMATION: Probe H

<400> SEQUENCE: 48
ccgtttacag cagtacaaat ggcagtattc aaaacgg                              37

<210> SEQ ID NO 49
<211> LENGTH: 46
<212> TYPE: DNA
<213> ORGANISM: Artificial Sequence
<220> FEATURE:
<223> OTHER INFORMATION: Probe I

<400> SEQUENCE: 49
cacagcagta caaatggcag tattcatcca caattttaat gctgtg                    46

<210> SEQ ID NO 50
<211> LENGTH: 31
<212> TYPE: DNA
<213> ORGANISM: Artificial Sequence
<220> FEATURE:
<223> OTHER INFORMATION: Probe J

<400> SEQUENCE: 50
cttactcaca attttaaaag aaaagagtaa g                                    31

<210> SEQ ID NO 51
<211> LENGTH: 32
<212> TYPE: DNA
<213> ORGANISM: Artificial Sequence
<220> FEATURE:
<223> OTHER INFORMATION: Probe K

<400> SEQUENCE: 51
cttactcaca attttaaaag aaaaggagta ag                                   32

<210> SEQ ID NO 52
<211> LENGTH: 33
<212> TYPE: DNA
<213> ORGANISM: Artificial Sequence
<220> FEATURE:
<223> OTHER INFORMATION: Probe L

<400> SEQUENCE: 52
ctgactcaca attttaaaag aaaagggagt cag                                  33

<210> SEQ ID NO 53
<211> LENGTH: 28
<212> TYPE: DNA
<213> ORGANISM: Artificial Sequence
<220> FEATURE:
<223> OTHER INFORMATION: Probe M

<400> SEQUENCE: 53
gtaccacaat tttaaaagaa aagggtac                                        28
```

```
<210> SEQ ID NO 54
<211> LENGTH: 31
<212> TYPE: DNA
<213> ORGANISM: Artificial Sequence
<220> FEATURE:
<223> OTHER INFORMATION: Probe O

<400> SEQUENCE: 54
acgcctaatt ttcgggttta ttacagggcg t                              31

<210> SEQ ID NO 55
<211> LENGTH: 27
<212> TYPE: DNA
<213> ORGANISM: Artificial Sequence
<220> FEATURE:
<223> OTHER INFORMATION: Probe P

<400> SEQUENCE: 55
catcctttgg aaaggaccag caggatg                                   27

<210> SEQ ID NO 56
<211> LENGTH: 33
<212> TYPE: DNA
<213> ORGANISM: Artificial Sequence
<220> FEATURE:
<223> OTHER INFORMATION: Probe Q

<400> SEQUENCE: 56
caccctctgg aaaggtgaag gggcagtagg gtg                            33

<210> SEQ ID NO 57
<211> LENGTH: 30
<212> TYPE: DNA
<213> ORGANISM: Artificial Sequence
<220> FEATURE:
<223> OTHER INFORMATION: Probe R

<400> SEQUENCE: 57
tcgacaaagg tgaaggggca gtagtgtcga                                30

<210> SEQ ID NO 58
<211> LENGTH: 28
<212> TYPE: DNA
<213> ORGANISM: Artificial Sequence
<220> FEATURE:
<223> OTHER INFORMATION: Probe A1
<221> NAME/KEY: misc_feature
<222> LOCATION: (17)...(17)
<223> OTHER INFORMATION: N = Indole at position 17

<400> SEQUENCE: 58
gcgagacagc agtacanatg gcactcgc                                  28

<210> SEQ ID NO 59
<211> LENGTH: 26
<212> TYPE: DNA
<213> ORGANISM: Artificial Sequence
<220> FEATURE:
<223> OTHER INFORMATION: Probe B1
<221> NAME/KEY: misc_feature
<222> LOCATION: (16)...(16)
<223> OTHER INFORMATION: N = Indole at position 16

<400> SEQUENCE: 59
cggaacagca gtacanatgg catccg                                    26
```

-continued

```
<210> SEQ ID NO 60
<211> LENGTH: 26
<212> TYPE: DNA
<213> ORGANISM: Artificial Sequence
<220> FEATURE:
<223> OTHER INFORMATION: Probe E1
<221> NAME/KEY: misc_feature
<222> LOCATION: (14)...(14)
<223> OTHER INFORMATION: N = Indole at position 14

<400> SEQUENCE: 60
ccacagcagt acanatggca gtgtgg                                    26

<210> SEQ ID NO 61
<211> LENGTH: 37
<212> TYPE: DNA
<213> ORGANISM: Artificial Sequence
<220> FEATURE:
<223> OTHER INFORMATION: Probe H1
<221> NAME/KEY: misc_feature
<222> LOCATION: (18)...(18)
<223> OTHER INFORMATION: N = Indole at position 18

<400> SEQUENCE: 61
ccgtttacag cagtacanat ggcagtattc aaaacgg                        37

<210> SEQ ID NO 62
<211> LENGTH: 26
<212> TYPE: DNA
<213> ORGANISM: Artificial Sequence
<220> FEATURE:
<223> OTHER INFORMATION: Probe Eino
<221> NAME/KEY: misc_feature
<222> LOCATION: (14)...(14)
<223> OTHER INFORMATION: N = Inosine at position 14

<400> SEQUENCE: 62
ccacagcagt acanatggca gtgtgg                                    26

<210> SEQ ID NO 63
<211> LENGTH: 37
<212> TYPE: DNA
<213> ORGANISM: Artificial Sequence
<220> FEATURE:
<223> OTHER INFORMATION: Probe Hino
<221> NAME/KEY: misc_feature
<222> LOCATION: (17)...(17)
<223> OTHER INFORMATION: N = Inosine at position 17

<400> SEQUENCE: 63
ccgtttacag cagtacanat ggcagtattc aaaacgg                        37

<210> SEQ ID NO 64
<211> LENGTH: 46
<212> TYPE: DNA
<213> ORGANISM: Artificial Sequence
<220> FEATURE:
<223> OTHER INFORMATION: Probe Iino
<221> NAME/KEY: misc_feature
<222> LOCATION: (28)...(28)
<223> OTHER INFORMATION: N = Inosine at position 28

<400> SEQUENCE: 64
cacagcagta caaatggcag tattcatnca caattttaat gctgtg              46

<210> SEQ ID NO 65
<211> LENGTH: 46
<212> TYPE: DNA
<213> ORGANISM: Artificial Sequence
```

```
<220> FEATURE:
<223> OTHER INFORMATION: Probe lino2
<221> NAME/KEY: misc_feature
<222> LOCATION: (13)...(13)
<223> OTHER INFORMATION: N = Inosine at position 13
<221> NAME/KEY: misc_feature
<222> LOCATION: (28)...(28)
<223> OTHER INFORMATION: N = Inosine at position 28

<400> SEQUENCE: 65
cacagcagta canatggcag tattcatnca caattttaat gctgtg            46

<210> SEQ ID NO 66
<211> LENGTH: 28
<212> TYPE: DNA
<213> ORGANISM: Artificial Sequence
<220> FEATURE:
<223> OTHER INFORMATION: Molecular Beacon Probe

<400> SEQUENCE: 66
gcgagacgag ttcatgaggg cagctcgc                                28

<210> SEQ ID NO 67
<211> LENGTH: 189
<212> TYPE: DNA
<213> ORGANISM: Artificial Sequence
<220> FEATURE:
<223> OTHER INFORMATION: Target Sequence

<400> SEQUENCE: 67
attccctaca atccccaaag tcaaggagta gtagaatcta tgaataaaga attaaagaaa     60
attataggac aggtaagaga tcaggctgaa catcttaagt tgcagctgca agaaggatcg   120
ttgaagctga cgagttcatg agggcaggcc gctatgatga aggggggatt gggggtaca   180 gtgcagggg                                                          189
```